(12) United States Patent
Hones et al.

(10) Patent No.: US 11,914,228 B2
(45) Date of Patent: Feb. 27, 2024

(54) OPHTHALMIC LENSES WITH LIGHT SCATTERING FOR TREATING MYOPIA

(71) Applicant: SightGlass Vision, Inc., Palo Alto, CA (US)

(72) Inventors: Peter Hones, Menlo Park, CA (US); Thomas W. Chalberg, Jr., Menlo Park, CA (US)

(73) Assignee: SightGlass Vision, Inc., Palo Alto, CA (US)

( * ) Notice: Subject to any disclaimer, the term of this patent is extended or adjusted under 35 U.S.C. 154(b) by 660 days.

(21) Appl. No.: 17/141,055

(22) Filed: Jan. 4, 2021

(65) Prior Publication Data

US 2021/0165244 A1 Jun. 3, 2021

Related U.S. Application Data

(63) Continuation of application No. 16/236,961, filed on Dec. 31, 2018, now Pat. No. 10,884,264.
(Continued)

(51) Int. Cl.
*G02C 1/02* (2006.01)
*G02C 7/02* (2006.01)
(Continued)

(52) U.S. Cl.
CPC .............. *G02C 7/021* (2013.01); *G02C 7/027* (2013.01); *G02C 7/061* (2013.01); *G02C 7/10* (2013.01);
(Continued)

(58) Field of Classification Search
CPC ........ G02C 7/021; G02C 7/027; G02C 7/061; G02C 7/10; G02C 7/165; G02C 2202/24;
(Continued)

(56) References Cited

U.S. PATENT DOCUMENTS 149,270 A 3/1847 Watson
338,003 A 3/1886 Ward
(Continued)

FOREIGN PATENT DOCUMENTS

AU 2005289302 4/2006
CN 1909860 2/2007
(Continued)

OTHER PUBLICATIONS

Ahern "Biochemical, reagents kits offer scientists good return on investment," The Scientist, Jul. 1995, 9(15):20.
(Continued)

*Primary Examiner* — Tuyen Tra
(74) *Attorney, Agent, or Firm* — Fish & Richardson P.C.

(57) ABSTRACT

An ophthalmic lens that includes a lens material having two opposing curved surfaces, the curved surfaces defining a lens axis; and a light scattering region surrounding a clear aperture. The clear aperture and the light scattering region are substantially centered on the lens axis, and the light scattering region has a plurality of spaced apart scattering centers (e.g., on a lens surface and/or embedded in the lens material) sized and shaped to scatter incident light, the scattering centers being arranged in a pattern that includes a random variation in spacing between adjacent dots and/or a random variation in dot size.

20 Claims, 20 Drawing Sheets

Related U.S. Application Data

(60) Provisional application No. 62/671,992, filed on May 15, 2018, provisional application No. 62/663,938, filed on Apr. 27, 2018, provisional application No. 62/624,038, filed on Jan. 30, 2018.

(51) Int. Cl.
  *G02C 7/06* (2006.01)
  *G02C 7/10* (2006.01)
  *G02C 7/16* (2006.01)
  *A61B 3/117* (2006.01)

(52) U.S. Cl.
  CPC ............ *G02C 7/165* (2013.01); *A61B 3/1173* (2013.01); *G02C 2202/24* (2013.01)

(58) Field of Classification Search
  CPC . G02C 7/022; A61B 3/1173; B29D 11/00009; B29D 11/00326
  USPC ............... 351/159.01, 159.6, 159.69, 159.79
  See application file for complete search history.

(56) References Cited

U.S. PATENT DOCUMENTS

| | | |
|---|---|---|
| 506,983 A | 10/1893 | Diemmer et al. |
| 712,466 A | 10/1902 | Taylor |
| 1,959,915 A | 5/1934 | Guthrie |
| 3,507,566 A | 4/1970 | Knapp |
| 4,194,814 A | 3/1980 | Fischer et al. |
| 4,338,003 A | 7/1982 | Adrian |
| 4,704,016 A | 11/1987 | de Carle |
| 4,710,327 A | 12/1987 | Neefe |
| 4,889,421 A | 12/1989 | Cohen |
| 4,909,818 A | 3/1990 | Jones |
| 5,034,100 A | 7/1991 | Sides |
| 5,044,742 A | 9/1991 | Cohen |
| 5,116,112 A | 5/1992 | Rawlings |
| 5,260,727 A | 11/1993 | Oksman et al. |
| 5,585,968 A | 12/1996 | Guhman et al. |
| 5,800,992 A | 9/1998 | Fodor et al. |
| 5,837,461 A | 11/1998 | Neitz |
| 5,867,247 A | 2/1999 | Martin et al. |
| 5,905,561 A | 5/1999 | Lee et al. |
| 5,926,250 A | 7/1999 | Mukaiyama et al. |
| 6,149,270 A | 11/2000 | Hayashi |
| 6,343,861 B1 | 2/2002 | Kris et al. |
| 6,582,908 B2 | 6/2003 | Fodor et al. |
| 6,706,867 B1 | 3/2004 | Lorenz |
| 6,712,466 B2 | 3/2004 | Dreher |
| 6,712,467 B1 | 3/2004 | Kitani |
| 6,754,299 B2 | 6/2004 | Patch |
| 6,997,554 B2 | 2/2006 | Nakada et al. |
| 7,025,460 B2 | 4/2006 | Smitth et al. |
| 7,506,983 B2 | 3/2009 | To et al. |
| 7,604,351 B2 | 10/2009 | Fukuma et al. |
| 7,665,842 B2 | 2/2010 | Ho et al. |
| 7,766,482 B2 | 8/2010 | Smith et al. |
| 7,862,171 B2 | 1/2011 | Varnas et al. |
| 7,901,075 B2 | 3/2011 | Rooney et al. |
| 7,992,997 B2 | 8/2011 | Varnas |
| 7,997,727 B2 | 8/2011 | Ho et al. |
| 8,052,278 B2 | 11/2011 | Bovet |
| 8,057,034 B2 | 11/2011 | Ho et al. |
| 8,079,702 B2 | 12/2011 | Ballet |
| 8,115,792 B2 | 2/2012 | Petsch et al. |
| 8,162,477 B2 | 4/2012 | Carimalo et al. |
| 8,240,847 B2 | 8/2012 | Holden et al. |
| RE43,851 E | 12/2012 | To et al. |
| 8,342,684 B2 | 1/2013 | Ho et al. |
| 8,500,278 B2 | 8/2013 | Lo et al. |
| 8,540,365 B2 | 9/2013 | Varnas |
| 8,684,520 B2 | 4/2014 | Lindacher et al. |
| 8,690,319 B2 | 4/2014 | Menezes |
| 8,807,747 B2 | 8/2014 | Guilloux et al. |
| RE45,147 E | 9/2014 | To et al. |
| 8,833,936 B2 | 9/2014 | Varnas |
| 8,926,092 B2 | 1/2015 | Weeber |
| 8,931,897 B2 | 1/2015 | Holden et al. |
| 8,950,860 B2 | 2/2015 | Tse et al. |
| 8,951,729 B2 | 2/2015 | Neitz et al. |
| 8,992,010 B2 | 3/2015 | Ho et al. |
| 8,998,408 B2 | 4/2015 | Wei et al. |
| 9,360,683 B2 | 6/2016 | Buehren |
| 9,417,463 B2 | 8/2016 | Brennan et al. |
| 9,423,633 B2 | 8/2016 | Ho et al. |
| 9,547,182 B2 | 1/2017 | Collins et al. |
| 9,594,259 B2 | 3/2017 | Brennan et al. |
| 9,625,739 B2 | 4/2017 | Brennan et al. |
| 9,709,819 B2 | 7/2017 | Lippens et al. |
| 9,720,253 B2 | 8/2017 | Neitz et al. |
| 9,733,494 B2 | 8/2017 | Brennan et al. |
| 9,746,693 B2 | 8/2017 | Peloux et al. |
| 9,829,722 B2 | 11/2017 | Tse et al. |
| 10,012,849 B2 | 7/2018 | Collins et al. |
| RE47,006 E | 8/2018 | To et al. |
| 10,042,091 B2 | 8/2018 | Kildishev et al. |
| 10,061,143 B2 | 8/2018 | Brennan et al. |
| 10,156,737 B2 | 12/2018 | Martinez et al. |
| 10,203,522 B2 | 2/2019 | Bakaraju et al. |
| 10,231,897 B2 | 3/2019 | Tse et al. |
| 10,247,964 B2 | 4/2019 | Sankaridurg et al. |
| 10,302,962 B2 | 5/2019 | Neitz et al. |
| 10,429,670 B2 | 10/2019 | Newman |
| 10,571,717 B2 | 2/2020 | Neitz et al. |
| 10,787,707 B2 | 9/2020 | Neitz et al. |
| 10,795,181 B2 | 10/2020 | Neitz et al. |
| 10,884,264 B2 | 1/2021 | Hones et al. |
| 11,048,102 B2 | 6/2021 | Neitz |
| 11,543,681 B2 * | 1/2023 | Neitz ...................... G02C 7/04 |
| 2002/0140900 A1 | 10/2002 | Streibig |
| 2003/0082576 A1 | 5/2003 | Jones et al. |
| 2004/0110179 A1 | 6/2004 | Shuber |
| 2004/0150787 A1 | 8/2004 | Niculas |
| 2005/0208555 A1 | 9/2005 | Raimond |
| 2006/0082729 A1 | 4/2006 | To et al. |
| 2006/0118263 A1 | 6/2006 | Silvestrini |
| 2006/0235428 A1 | 10/2006 | Silvestrini |
| 2006/0285071 A1 | 12/2006 | Erickson et al. |
| 2007/0026167 A1 | 2/2007 | Bourdelais et al. |
| 2007/0115431 A1 | 5/2007 | Smith et al. |
| 2007/0247588 A1 | 10/2007 | Cano |
| 2007/0296916 A1 | 12/2007 | Holden et al. |
| 2008/0030675 A1 | 2/2008 | Dillon |
| 2008/0084534 A1 | 4/2008 | Lindacher et al. |
| 2008/0151183 A1 | 6/2008 | Altmann |
| 2008/0221674 A1 | 9/2008 | Blum et al. |
| 2008/0309882 A1 | 12/2008 | Thom et al. |
| 2009/0059168 A1 | 3/2009 | Miller et al. |
| 2009/0115962 A1 | 5/2009 | Bovet et al. |
| 2009/0257026 A1 | 10/2009 | Varnas et al. |
| 2010/0021889 A1 | 1/2010 | Juo |
| 2010/0091240 A1 | 4/2010 | Drobe et al. |
| 2010/0149488 A1 | 6/2010 | Lo et al. |
| 2011/0051079 A1 | 3/2011 | Martinez et al. |
| 2011/0194195 A1 | 8/2011 | Zalevsky et al. |
| 2011/0313058 A1 | 12/2011 | Neitz et al. |
| 2012/0014977 A1 | 1/2012 | Furihata |
| 2012/0062836 A1 | 3/2012 | Tse et al. |
| 2012/0182520 A1 | 7/2012 | Neitz et al. |
| 2013/0053425 A1 | 2/2013 | To et al. |
| 2013/0103147 A1 | 4/2013 | Christie et al. |
| 2013/0107206 A1 | 5/2013 | Slater |
| 2014/0080900 A1 | 3/2014 | Neitz et al. |
| 2014/0111763 A1 | 4/2014 | Griffin |
| 2015/0036102 A1 | 2/2015 | Ghosh et al. |
| 2015/0109574 A1 | 4/2015 | Tse et al. |
| 2015/0111782 A1 | 4/2015 | Neitz et al. |
| 2015/0160477 A1 | 6/2015 | Dai et al. |
| 2015/0316788 A1 | 11/2015 | Holden et al. |
| 2015/0331255 A1 | 11/2015 | Sankaridurg et al. |
| 2016/0026000 A1 | 1/2016 | Kester |
| 2016/0143801 A1 | 5/2016 | Lam et al. |
| 2016/0377884 A1 | 12/2016 | Lau et al. |

(56) References Cited

U.S. PATENT DOCUMENTS

| | | |
|---|---|---|
| 2017/0018916 A1 | 1/2017 | Itsuki et al. |
| 2017/0115509 A1 | 4/2017 | Brennan et al. |
| 2017/0131567 A1 | 5/2017 | To et al. |
| 2017/0168320 A1 | 6/2017 | Tsubota et al. |
| 2017/0184875 A1 | 6/2017 | Newman |
| 2017/0189168 A1 | 7/2017 | Zickler et al. |
| 2017/0192252 A1 | 7/2017 | Brennan et al. |
| 2017/0276963 A1 | 9/2017 | Brennan et al. |
| 2017/0292160 A1 | 10/2017 | Neitz et al. |
| 2017/0336653 A1 | 11/2017 | Bakaraju |
| 2018/0112268 A1 | 4/2018 | Neitz et al. |
| 2018/0275425 A1 | 9/2018 | Collins et al. |
| 2018/0275427 A1 | 9/2018 | Lau et al. |
| 2019/0033619 A1 | 1/2019 | Neitz et al. |
| 2019/0235279 A1 | 8/2019 | Hones et al. |
| 2019/0302477 A1 | 10/2019 | Neitz et al. |
| 2020/0073147 A1 | 3/2020 | Bakaraju et al. |
| 2020/0089023 A1 | 3/2020 | Zhou et al. |
| 2020/0271955 A1 | 8/2020 | Neitz et al. |
| 2020/0393699 A1 | 12/2020 | Neitz |
| 2021/0341753 A1 | 11/2021 | Neitz |
| 2022/0035179 A1 | 2/2022 | Rappon et al. |
| 2023/0107026 A1 | 4/2023 | Neitz et al. |
| 2023/0137646 A1 | 5/2023 | Neitz et al. |

FOREIGN PATENT DOCUMENTS

| | | |
|---|---|---|
| CN | 2924572 | 7/2007 |
| CN | 101198434 | 6/2008 |
| CN | 101273882 | 10/2008 |
| CN | 101595420 | 12/2009 |
| CN | 101730500 | 6/2010 |
| CN | 101268408 | 3/2011 |
| CN | 102238927 | 11/2011 |
| CN | 103097940 | 5/2013 |
| CN | 103959138 | 7/2014 |
| CN | 104094164 | 10/2014 |
| CN | 104094165 | 10/2014 |
| CN | 103293707 | 12/2014 |
| CN | 104656271 | 5/2015 |
| CN | 104678572 | 6/2015 |
| CN | 105378545 | 3/2016 |
| CN | 102892380 | 10/2016 |
| EP | 0457612 | 11/1991 |
| EP | 1042700 | 3/2002 |
| EP | 1799166 | 6/2007 |
| EP | 2131721 | 12/2009 |
| EP | 2616876 | 7/2013 |
| EP | 2962155 | 1/2016 |
| EP | 2548533 | 2/2018 |
| EP | 3614981 | 3/2020 |
| EP | 3667401 | 6/2020 |
| EP | 3746001 | 12/2020 |
| EP | 3931626 | 1/2022 |
| HK | 1210838 | 5/2016 |
| JP | S5829627 | 2/1983 |
| JP | 2004514921 | 5/2004 |
| JP | 2008040497 | 2/2008 |
| JP | 2008514318 | 5/2008 |
| JP | 2009-511962 | 3/2009 |
| JP | 4891249 | 3/2012 |
| JP | 2012-185348 | 9/2012 |
| JP | 2013537317 | 9/2013 |
| JP | 2017510851 | 4/2017 |
| JP | 2019529968 | 10/2019 |
| JP | 2012513252 | 7/2021 |
| KR | 100686551 | 2/2007 |
| KR | 100840845 | 6/2008 |
| TW | 279510 | 6/1996 |
| TW | I446830 | 7/2001 |
| TW | 201211618 | 3/2012 |
| TW | I370278 | 8/2012 |
| TW | 201307942 | 2/2013 |
| TW | I493240 | 7/2015 |
| TW | I530727 | 4/2016 |
| TW | I559044 | 11/2016 |
| TW | I561885 | 12/2016 |
| WO | WO1986/006846 | 11/1986 |
| WO | WO1997/031286 | 8/1997 |
| WO | WO1999/066366 | 12/1999 |
| WO | WO2000/052516 | 9/2000 |
| WO | WO2002/031585 | 4/2002 |
| WO | WO2006/034652 | 4/2006 |
| WO | WO2006/113149 | 10/2006 |
| WO | WO2007/082268 | 7/2007 |
| WO | WO2007/132834 | 11/2007 |
| WO | WO2008/026674 | 3/2008 |
| WO | WO2008/045847 | 4/2008 |
| WO | WO2008/059178 | 5/2008 |
| WO | WO2008/083418 | 7/2008 |
| WO | WO2010/019397 | 2/2010 |
| WO | WO2010/075319 | 7/2010 |
| WO | WO2010/088644 | 8/2010 |
| WO | WO2011/031948 | 3/2011 |
| WO | WO2012/034265 | 3/2012 |
| WO | WO2012/097213 | 7/2012 |
| WO | WO2013/015743 | 1/2013 |
| WO | WO2013/082545 | 6/2013 |
| WO | WO2013/134825 | 9/2013 |
| WO | WO2014/194444 | 12/2014 |
| WO | WO2015/055322 | 4/2015 |
| WO | WO2015/147758 | 10/2015 |
| WO | WO2015/186723 | 12/2015 |
| WO | WO2016/138512 | 9/2016 |
| WO | WO2017/178430 | 10/2017 |
| WO | WO2018/026697 | 2/2018 |
| WO | WO2018/076057 | 5/2018 |
| WO | WO2018/208724 | 11/2018 |
| WO | WO2019/166653 | 9/2019 |
| WO | WO2020/138127 | 7/2020 |

OTHER PUBLICATIONS

Applied Biosystems—Product Bulletin—Automated DNA Sequencing [online] "Abi Prism® BigDyeTM Primer Sequencing Kit," 2000, available via url: <tools.thermofisher.com/content/sfs/brochures/cms_040730.pdf>, 4 pages.

Carkeet et al., "Repeatability of IOLMaster Biometry in Children, Optometry and Vision Science", Nov. 2004, 81(11) : 829-834.

Carroll et al, "Estimates of L:M cone ratio from ERG flicker photometry and genetics", Journal of Vision, 2002, 2(8):531-542.

Carroll et al., "Cone photoreceptor mosaic disruption associated with Cys203Arg mutation in the M-cone opsin," Proceedings of the National Academy of Sciences of the United States of America, 2009, 106(49):20948-20953.

Carroll, et al., "Functional photoreceptor loss revealed with adaptive optics: An alternate cause of color blindness," Proceedings of the National Academy of Sciences of the United States of America, 2004, 101(22):8461-8466.

Carroll, J., McMahon, C., Neitz, M., & Neitz, J. (2000). Flicker-photometric electroretinogram estimates of L: M cone photoreceptor ratio in men with photopigment spectra derived from genetics. Journal of The Optical Society of America A, 17,499-509.

Crognale et al., "Characterization of a novel form of X-linked incomplete achromatopsia", Visual Neuroscience, 2004, 21(3):197-203.

Davidoff, "Cone opsin gene variants in color blindness and other vision disorders," 2015, Retrieved from the Internet: <https://digital.lib.washington.edu/researchworks/bitstream/handle/1773/33578/Davidoff_washington_0250E_15133.pdf?sequence=1&isAllowed=y>, 132 pages.

Drummond-Borg, et al., "Molecular patterns of X chromosome-linked color vision genes among 134 men of European ancestry," Proceedings of the National Academy of Sciences of the United States of America, Feb. 1989, 86:983-987.

EP Extended European Search Report in European Appln. No. 19747437.2, dated Mar. 16, 2021, 10 pages.

Gardner et al, "Three Different Cone Opsin Gene Array Mutational Mechanisms with Genotype-Phenotype Correlation and Functional Investigation of Cone Opsin Variants" Human Mutation (2014) vol. 35(11), pp. 1354-1362.

(56) References Cited

OTHER PUBLICATIONS

GeneCards [online], "GeneCard for the OPN1MW gene", retrieved on Apr. 6, 2020, retrieved from <genecards.org/cgi-bin/carddisp_pl?gene=OPN1MW>, 27 pages.
Greenwald et al., "Role of a Dual Splicing and Amino Acid Code in Myopia, Cone Dysfunction and Cone Dystrophy Associated with L/M Opsin Interchange Mutations," Translation Vision Science & Technology, vol. 6, No. 3, dated May 10, 2017, 19 pages.
Gunther et al., "Individual differences in chromatic (red/green) contrast sensitivity are constrained by the relative number of L-versus M-cones in the eye", Vision Research, May 2002, 42(11):1367-1378.
Gwiazda et al., "A Randomized Clinical Trial of Progressive Addition Lenses versus Single Vision Lenses on the Progression of Myopia in Children", Investigative Ophthalmology & Visual Science, Apr. 2003, 44:1492-1500.
Hahner et al., "Strategies for SNP genotyping by mass spectrometry", International Congress Series, Jan. 2003, 1239: 11-16.
Halushka et al., "Patterns of single-nucleotide polymorphisms in candidate genes for blood-pressure homeostasis", Nat Genet, 1999, 239-247.
HattersleyDM et al., "What makes a good genetic association study?" The Lancet, Oct. 2005, 366(9493):1315-1323.
Hirschhorn et al. "A comprehensive review of genetic association studies", Genet Med, 2002, 45-61.
Hofer, et al., "Organization of the Human Trichromatic Cone Mosaic" Journal of Neuroscience, Oct. 19, 2005, 25(42):9669-9679.
JP Office Action in Japanese Appln. No. 2020-541739, dated Sep. 13, 2021, 19 pages (with translation).
Kuchenbecker et al, "Topography of the long- to middle-wavelength sensitive cone ratio in the human retina assessed with a wide-field color multifocal electroretinogram", Vis Neurosci, May-Jun. 2008, 25(3):301-6.
Lucentini, "Gene association studies typically wrong: reproducible gene-disease associations are few and far between", The Scientist, 2004, 18(24): p. 20.
McClements, Michelle et al. Variations in Opsin Coding Sequences Cause X-Linked Cone Dysfunction Syndrome, with Myopia and Dichromacy Investigative Ophthalmology & Visual Science (2013) vol. 54(2), pp. 1361-1369.
McMahon et al., "The L:M cone ratio in males of African descent with normal color vision", Journal of Vision, 2008, 8(2):1-9.
Michaelides et al., "X-Linked Cone Dysfunction Syndrome with Myopia and Protanopia" Ophthalmology, Aug. 2005, 112(8): 1448-1454.
Michaelides, et al. (2010) "The PROM1 mutation p.R373C causes an autosomal dominant bull's eye maculopathy associated with rod, rod-cone, and macular dystrophy," IOVS, 51(9): 4771-4780.
Mizrahi-Meissonnier et al., "Variable Retinal Phenotypes Caused by Mutations in the X-Linked Photopigment Gene Array", Investigative Ophthalmology & Visual Science, Aug. 2010, (51):3884-3892.
Montana.edu [online] "Optical System Design—S15," retrieved on Jan. 7, 2019, retrieved from <http://www.montana.edu/jshaw/documents/18%20EELE582_S15_OTFMTF.pdf>, 18 pages.
Mummidi et al., "Evolution of Human and Non-human Primate CC Chemokine Receptor 5 Gene and mRNA, Potential Roles for Haplotype and mRNA Diversity, Differential Haplotype-Specific Transcriptional Activity, and Altered Transcription Factor Binding to Polymorphic Nucleotides in the Pathogenesis of HIV-1 and Simian Immunodeficiency Virus*210", Journal of Biological Chemistry, 2000, 275(25):18946-18961.
Nathans et al., "Molecular Genetics of Human Blue Cone Monochromacy", Aug. 1989, 45(4920): pp. 831-838.
Nathans et al., "Molecular Genetics of Inherited Variation in Human Color Vision", Apr. 1986, 232(4747): pp. 203-210.
NCBI Database GenBank Accession No. NM 020061. Nov. 1, 2009. National Center for Biotechnology Information, National Library of Medicine, Bethesda, MD, USA), 7 pages.

Neitz et al. "Variety of genotypes in males diagnosed as dichromatic on a conventional clinical anomaloscope", Visual Neuroscience, 2004, 21(3):205-216.
Neitz et al., "Cone mosaic disruption caused by L/M opsin mutations in bornholm eye disease," ARVO Annual Meeting Abstract, Apr. 2011, 2 pages.
Neitz et al., "Polymorphism in the number of genes encoding long-wavelength-sensitive cone pigments among males with normal color vision", Vision Research, Sep. 1995, 35(17): 2395-2407.
Neitz, "A new mass screening test for color-vision deficiencies in children" Color Research & Application, 2001, 26(1): S239-S249.
Oda, et al. (2003) "Analysis of L-cone/M-cone visual pigment gene arrays in females by long-range PCR" Visior Research, vol. 43, pp. 489-495.
Okada et al., "Target Spatial Frequency Determines the Response to Conflicting Defocus- and Convergence-Driven Accommodative Stimuli," 2006, Elsevier, vol. 46, pp. 475-484.
PCT International Preliminary Report on Patentability and Written Opinion in International Application No. PCT/US2019/015724, dated Aug. 13, 2020, 7 pages.
PCT International Search Report and Written Opinion in International Appln. PCT/US19/15724, dated Jun. 7, 2019, 10 pages.
Radhakrishna, et al., "The 'X-linked' severe form of myopia locus at Xq28 (MYP1): Narrowing of the critical region and exclusion of twelve known genes localized in the interval.", ARVO Annual Meeting Abstract, May 2005, 1 page.
Scholl, et al., (2001) "Macular dystrophy with protan genotype and phenotype studied with cone type specific ERGs" Current Eye Research, vol. 22(3) pp. 221-228.
Scholl, et al., (2006) "Progressive cone dystrophy with deutan genotype and phenotype", Graefe's Arch Clin Exp Ophthalmol, vol. 244, pp. 183-191.
Schwartz et al., "X-linked myopia: Bornholm Eye Disease", Clinical Genetics, 1990, 38(4):281-286.
slrlounge.com [online] "Diffraction, Aperture, and Starburst Effects," dated Feb. 9, 2011, [Retrived on Jan. 7, 2019] Retrieved from: https://www.slrlounge.com/diffraction-aperture-and-starburst-effects/, 11 pages.
TW Office Action in Taiwanese Appln. No. 108103396, dated Dec. 18, 2019, 6 pages (with English translation).
TW Office Action in Taiwanese Appln. No. 108103396, dated Sep. 10, 2019, 32 pages (with English translation).
TW Office Action in Taiwanese Appln. No. 109123077, dated Feb. 17, 2021, 6 pages (with English translation).
Twelker et al., "Children's Ocular Components and Age, Gender, and Ethnicity", Optometry and Vision Science, Aug. 2009, 86(8):918-935.
Ueyama, Hisao et al. "Unique haplotype in exon 3 of cone opsin mRNA affects splicing of its precursor, leading to congenital color vision defect" Biochemical and Biophysical Research Communications (2012) vol. 424, pp. 152-157.
Verrelli et al., "Signatures of Selection and Gene Conversion Associated with Human Color Vision Variation", The American Journal of Human Genetics, 2004,75(3): 363-375.
Winderickx et al., "Defective colour vision associated with a missense mutation in the human green visual pigment gene", Nat Genet 1992, 251-256.
Winderickx, et al. (1993) "Haplotype diversity in the human red and green opsin genes: evidence for frequent sequence exchange in exon 3," Human Molecular Genetics, 2(9):1413-1421.
Young et al., "X-Linked High Myopia Associated With Cone Dysfunction", Arch Ophthalmol. 2004, 122(6):897-908.
Young, et al., (2001) "Further refinement of the MYP2 locus for autosomal dominant high myopia by linkage disequilibrium analysis", Ophthalmic Genetics, vol. 22, pp. 69-75.
Anstice et al., "Effect of dual-focus soft contact lens wear on axial myopia progression in children," Ophthalmology, 2011, 1152-1161.
Brennan et al., "Commonly held beliefs about myopia that lack a robust evidence base," Eye & Contact Lens, Jul. 2019, 45(4):215-225.
Chamberlain et al., "A 3-year Randomized Clinical Trial of MiSight Lenses for Myopia Control", Optom Vis Sci, 2019, 96(8): 556-567.

(56) References Cited

OTHER PUBLICATIONS

Cheng et al., "Effect of Bifocal and Prismatic Bifocal Spectacles on Myopia Progression in Children: Three-Year Results of a Randomized Clinical Trial", JAMA Ophthalmology, Mar. 2014, 132(3):258-264.

Cheng et al., "Soft contact lenses with positive spherical aberration for myopia control," Optometry and Vision Science, Apr. 2016, 93(4):353-366.

Jones et al., "The Prevalence and Impact of High Myopia," Eye & Contact Lens, May 2012, 38(3):188-96.

Ruiz-Pomeda et al., "MiSight Assessment Study Spain (MASS). A 2-year randomized clinical trial," Graefe's Archive for Clinical and Experimental Ophthalmology, Feb. 3, 2018, 256:1011-1021.

Sankaridurg et al., "Decrease in rate of myopia progression with a contact lens designed toreduce relative peripheral huperopia: One-year results," IOVS, Dec. 2011, 52(13):9362-9367.

Tedja et al., "Genome-wide association meta-analysis highlights light-induced signaling as a driver for refractive error", Nature Genetics, Jun. 2018, 50(6):834-848.

Vitale et al, "Increased prevalence of myopia in the United States between 1971-1972 and 1999-2004," Arch Ophthalmol., Dec. 2009, 127(12):1632-1639.

Zhang, "Genetics of Refraction and Myopia", Progress in Molecular Biology and Translational Science, 2015, 134: 269-279.

\* cited by examiner

FIG. 2

OPHTHALMIC LENSES WITH LIGHT SCATTERING FOR TREATING MYOPIA

CROSS-REFERENCE TO RELATED APPLICATIONS

This application is a continuation of and claims priority to U.S. patent application Ser. No. 16/236,961, filed Dec. 31, 2018, which claims priority to Provisional Application No. 62/624,038, entitled "METHODS FOR FORMING OPHTHALMIC LENSES FOR TREATING MYOPIA," filed on Jan. 30, 2018, to Provisional Application No. 62/663,938, entitled "OPHTHALMIC LENSES WITH LIGHT SCATTERING FOR TREATING MYOPIA," filed on Apr. 27, 2018, and to Provisional Application No. 62/671,992, entitled "OPHTHALMIC LENSES WITH LIGHT SCATTERING FOR TREATING MYOPIA," filed on May 15, 2018. The entire contents of each of these applications is incorporated herein by reference.

FIELD OF THE INVENTION

The invention features ophthalmic lenses for treating myopia and reducing myopia progression.

BACKGROUND

The eye is an optical sensor in which light from external sources is focused, by a lens, onto the surface of the retina, an array of wavelength-dependent photosensors. Each of the various shapes that the eye lens can adopt is associated with a focal length at which external light rays are optimally or near-optimally focused to produce inverted images on the surface of the retina that correspond to external images observed by the eye. The eye lens, in each of the various shapes that the eye lens can adopt, optimally or near-optimally, focuses light emitted by, or reflected from external objects that lie within a certain range of distances from the eye, and less optimally focuses, or fails to focus objects that lie outside that range of distances.

In normal-sighted individuals, the axial length of the eye, or distance from the lens to the surface of the retina, corresponds to a focal length for near-optimal focusing of distant objects. The eyes of normal-sighted individuals focus distant objects without nervous input to muscles which apply forces to alter the shape of the eye lens, a process referred to as "accommodation" Closer, nearby objects are focused, by normal individuals, as a result of accommodation.

Many people, however, suffer from eye-length-related disorders, such as myopia ("nearsightedness"). In myopic individuals, the axial length of the eye is longer than the axial length required to focus distant objects without accommodation. As a result, myopic individuals can view near objects clearly, but objects further away are blurry. While myopic individuals are generally capable of accommodation, the average distance at which they can focus objects is shorter than that for normal-sighted individuals.

Typically, infants are born hyperopic, with eye lengths shorter than needed for optimal or near-optimal focusing of distant objects without accommodation. During normal development of the eye, referred to as "emmetropization," the axial length of the eye, relative to other dimensions of the eye, increases up to a length that provides near-optimal focusing of distant objects without accommodation. Ideally, biological processes maintain the near-optimal relative eye length to eye size as the eye grows to final, adult size. However, in myopic individuals, the relative axial length of the eye to overall eye size continues to increase during development, past a length that provides near-optimal focusing of distant objects, leading to increasingly pronounced myopia.

It is believed that myopia is affected by behavioral factors as well as genetic factors. Accordingly, myopia may be mitigated by therapeutic devices which address behavioral factors. For example, therapeutic devices for treating eye-length related disorders, including myopia, are described in U.S. Pub. No. 2011/0313058A1.

SUMMARY

Eyeglasses and contact lenses are disclosed that reduce signals in the retina responsible for growth of eye length. Exemplary embodiments are made using, e.g., polycarbonate or Trivex lens blanks which have been treated by applying a pattern of scattering centers, or "dots," with an aperture free of dots on the viewing axis. The result is a reduction in contrast in a retinal image which is believed to reduce eye growth associated with myopia progression. The apertures free from dots located on the lens axis allows a user to experience maximal visual acuity when viewing on-axis objects, while objects in the periphery of the user's visual field are viewed with reduced contrast and acuity.

For these eyeglasses, the focused image is reduced in contrast in the peripheral area of the retina compared to that normally used to correct (but not treat) refractive errors. The exact amount of contrast reduction depends on the relative amount of dark and light areas in the image being transmitted. For the example above, where 24% of the light is dispersed uniformly, the maximum contrast reduction would be 48% where contrast is defined as the Luminance difference/Average luminance. Experiments demonstrate that this amount of reduction in contrast in the peripheral area of the retina has significant effects on the physiology of the eye related to mechanisms responsible for controlling the growth of eye length.

Various aspects of the invention are summarized as follows:

In general, in a first aspect, the invention features an ophthalmic lens that includes a lens material having two opposing curved surfaces; and a scattering region surrounding a clear aperture, wherein the scattering region has a plurality of spaced apart scattering centers sized and shaped to scatter incident light, the scattering centers being arranged in a pattern that includes an irregular variation in spacing between adjacent scattering centers and/or an irregular variation in scattering centers size.

Embodiments of the ophthalmic lens can include one or more of the following features and/or features of other aspects. For example, the scattering centers can be positioned relative to a regular array of lattice cites, wherein each scattering center is displaced in at least one dimension (e.g., x- and/or y-directions) from a corresponding one of the lattice sites by an amount equal to or less than a jitter amplitude, the jitter amplitude being a fraction of the distance between adjacent lattice sites. The jitter amplitude can be 0.5 or less (e.g., 0.01 to 0.5, 0.02 or more, 0.03 or more, 0.04 or more, 0.05 or more, 0.08 or more, 0.1 or more, 0.12 or more, 0.15 or more, 0.18 or more, 0.2 or more, 0.25 or more, 0.3 or more, 0.35 or more, 0.4 or more).

The scattering centers can have a dimension that varies randomly from a nominal value, the random variation being equal to or less than a jitter amplitude. The jitter amplitude can be 0.5 times the nominal value or less (e.g., 0.01 to 0.5, 0.02 or more, 0.03 or more, 0.04 or more, 0.05 or more, 0.08 or more, 0.1 or more, 0.12 or more, 0.15 or more, 0.18 or more, 0.2 or more, 0.25 or more, 0.3 or more, 0.35 or more, 0.4 or more).

The scattering centers can have a volume that varies randomly from a nominal volume, the random variation being equal to or less than a jitter amplitude. The jitter amplitude times the nominal volume can be 0.5 or less (e.g., 0.01 to 0.5, 0.02 or more, 0.03 or more, 0.04 or more, 0.05 or more, 0.08 or more, 0.1 or more, 0.12 or more, 0.15 or more, 0.18 or more, 0.2 or more, 0.25 or more, 0.3 or more, 0.35 or more, 0.4 or more).

The lens can have a lens axis and the aperture and annular region are substantially centered on the lens axis.

The scattering region can include a first scattering area and a second scattering area arranged between the clear aperture and the first scattering area, the second scattering area comprising scattering centers sized and arranged to scatter incident light more weakly than the scattering centers of the first scattering area. The lens can have a lens axis and the aperture and first and second scattering areas are substantially centered on the lens axis, and the scattering centers in the second scattering area have a dimension that increases monotonically (e.g., linearly or geometrically) with increasing radial distance from the lens axis. The lens can have a lens axis and the aperture and first and second scattering areas are substantially centered on the lens axis, and the scattering centers in the second scattering area have a dimension and/or a volume that varies monotonically (e.g., linearly or geometrically) with increasing radial distance from the lens axis.

The irregular variations in scattering centers spacing can be random variations. The irregular variations in scattering center size can be random variations.

The scattering centers spacing and/or scattering centers sizes can be varied to encode information into the scattering centers.

The scattering centers can be substantially circular in shape. The scattering centers can be shaped as a logo or alphanumeric symbol.

The lens can be a plano lens, a single vision lens, or a multivision lens. The lens can be an eyeglass lens or a contact lens.

The scattering region can be an annular region. The clear aperture can be a circular aperture.

In another aspect, the invention features a method of treating eye-length related disorders, including: identifying, in a patient, an eye-length related disorder; and reducing a contrast of images in a periphery of the patient's vision using an ophthalmic lens according to the prior aspect.

In a further aspect, the invention features a pair of eyeglasses, including: eyeglass frames; and a pair of ophthalmic lenses each according to the foregoing aspects mounted in the frames.

Embodiments of the eyeglasses can include one or more of the following features and/or features of other aspects. For example, the dot pattern can reduce an image contrast of an object viewed through the dot pattern by at least 30% (e.g., at least 35%, at least 40%, at least 45%, at least 50%, at least 55%, at least 60%, up to 80%) compared to an image contrast of the object viewed through the clear aperture.

The lenses can have optical power to correct a wearer's on-axis vision to 20/20 or better through the clear aperture, and, for at least a portion of the wearer's peripheral vision through the dot pattern, the lenses correct the wearer's vision to 20/25 or better.

In another aspect, the invention features a method of treating eye-length related disorders, including identifying, in a patient, an eye-length related disorder; and reducing a contrast of images in a periphery of the patient's vision using foregoing eyeglasses.

In general, yet another aspect, the invention features a method, including: focusing a laser beam to a focal point; exposing an ophthalmic lens to the focused laser radiation to form optically scattering features in a pattern on a curved surface of the ophthalmic lens. Exposing the ophthalmic lens includes causing relative motion between the laser beam and the lens so that different locations of the lens surface intersect the laser beam at different locations with respect to the focal point.

Implementations of the method can include one or more of the following features and/or features of other aspects. For example, the optically scattering features formed by the laser beam can vary depending on the location of the lens surface with respect to the focal point. The degree of scattering due to an optically scattering feature can decrease as the distance of the lens surface with respect to the focal point increases.

The pattern can include an annular region of optically scattering features surrounding a clear aperture corresponding with a viewing axis of the ophthalmic lens. The optically scattering features can include discrete dots. The dots can be arranged in an array, each being spaced apart by a distance of 1 mm or less, each dot having a maximum dimension of 0.5 mm or less. The clear aperture can be an area free of dots having a maximum dimension of more than 1 mm.

The laser can be an infrared laser. The laser can be a $CO_2$ laser.

The ophthalmic lens can be exposed to pulsed laser radiation.

The laser can have sufficient energy to remove lens material from the surface of the lens.

The laser can have a power in a range from 0.5 W to 60 W.

The laser radiation can be focused to a spot size of about 0.1 mm or less (e.g., about 0.05 mm or less, about 0.025 mm or less) during the exposing.

The ophthalmic lens can be exposed so that each location exposed at the lens surface experiences a corresponding discrete exposure of the same duration and the same energy.

The exposed surface can be a convex surface or a concave surface.

In general, in a further aspect, the invention features a method of forming scattering centers in an ophthalmic lens, including: exposing an area of the ophthalmic lens to laser radiation having a wavelength and power sufficient to cause a material forming the ophthalmic lens to foam. Bubbles from the foam form scattering centers in the ophthalmic lens. Implementations of the method can include one or more features of other aspects.

In general, in yet another aspect, the invention features a method, including: simultaneously exposing an ophthalmic lens formed from a lens material to two or more beams of laser radiation such that the two or more beams overlap in a portion of the lens material, the intensity of the laser radiation in the overlapping beams being sufficient to form an optically scattering feature in the lens material; and varying the location of the overlapping beams in the lens to form a pattern of optically scattering features in the lens.

Implementations of the method can include one or more of the following features and/or features of other aspects. For example, the laser intensity of a single one of the two or more beams can be insufficient to form an optically scattering feature in the lens material in less than 10 seconds of exposure to the laser beam.

The laser radiation in the overlapping beams can interact with the lens material to change a refractive index of the lens material.

The laser radiation in the overlapping beams can change the refractive index of the lens material by causing a photochemical change in the lens material.

The laser radiation in the overlapping beams can change the refractive index of the lens material by causing a photothermal change in the lens material.

In another aspect, the invention features a pair of eyeglasses, that includes eyeglass frames and a pair of ophthalmic lenses mounted in the frames, the lenses each including a pattern distributed across each lens formed using one of the foregoing methods.

Embodiments of the eyeglasses can include one or more of the following features and/or features of other aspects. For example, each pattern can include an area including the optically scattering features surrounding a clear aperture devoid of scattering features. The dot pattern can reduce an image contrast of an object viewed through the dot pattern by at least 30% (e.g., by at least 35%, by at least 40%, by at least 45%, by at least 50%, by at least 55%, by at least 60%) compared to an image contrast of the object viewed through the clear aperture.

The lenses can have optical power to correct a wearer's on-axis vision to 20/20 or better through the clear aperture, and, for at least a portion of the wearer's peripheral vision through the dot pattern, the lenses correct the wearer's vision to 20/25 or better.

Among other advantages, disclosed embodiments feature eyeglasses that include features that reduce signals in the retina responsible for growth of eye length on the lenses for both eyes, without diminishing the user's on-axis vision in either eye to an extent that is disruptive to the user. For example, providing a dot pattern that modestly blurs the wearer's peripheral vision while allowing normal on-axis viewing through a clear aperture allows for all-day, everyday use by the wearer. Disclosed embodiments can also provide therapeutic benefits to a user in both eyes using only a single pair of eyeglasses, in contrast to approaches which involve alternating use of different pairs of eyeglasses or to using eyeglass attachments.

Moreover, the dot patterns can be largely unnoticeable to others, particularly where dot patterns are clear and colorless and/or where contact lenses are used. The subtlety of the dot patterns can result in more consistent use by certain wearers, especially children, who may otherwise be self-conscious during everyday (e.g., at school or otherwise among peers) use of more conspicuous devices. For example, graded dot patterns can be used to reduce conspicuity of dot patterns to third parties.

Dot patterns can also be optimized for viewer comfort. For example, dot patterns can feature a transition zone which softens the transition from the lens's clear aperture to the scattering zone in the viewer's visual field. Alternatively, or additionally, random jitter can be applied to dot patterns (e.g., to the dot size and/or dot spacing). Such randomization can reduce undesirable optical effects associated with uniform arrays of optical features (e.g., diffractive or interference effects). For instance, random jitter can be used to reduce glare experience by the user. It can also reduce conspicuity of dot patterns to third parties by reducing diffractive or interference effects in reflection.

Information can be encoded into dot patterns. For example, dots can be shaped as symbols (e.g., alphanumeric symbols) or logos. Alternatively, or additionally, dot shapes, sizes, and/or spacing can be varied according to a key to embed information into the dot pattern.

Disclosed embodiments can allow dot patterns for mitigating eye lengthening to be efficiently and economically formed on conventional ophthalmic lenses, for example by forming dot patterns on a surface or in the bulk of the lens.

BRIEF DESCRIPTION OF THE DRAWINGS

FIG. 2 illustrates contrast reduction experienced using exemplary ophthalmic lenses for treating myopia.

DETAILED DESCRIPTION

Figure 1B:
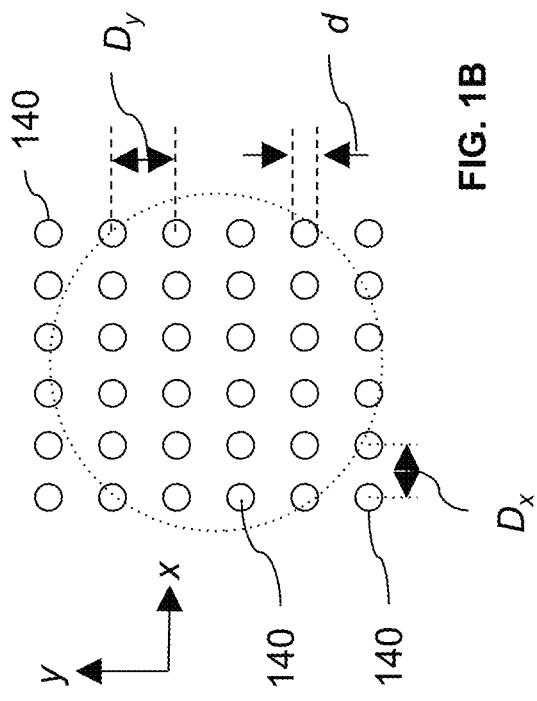
FIG. 1B shows a dot pattern on the ophthalmic lenses shown in FIG. 1A.
Figure 1A:
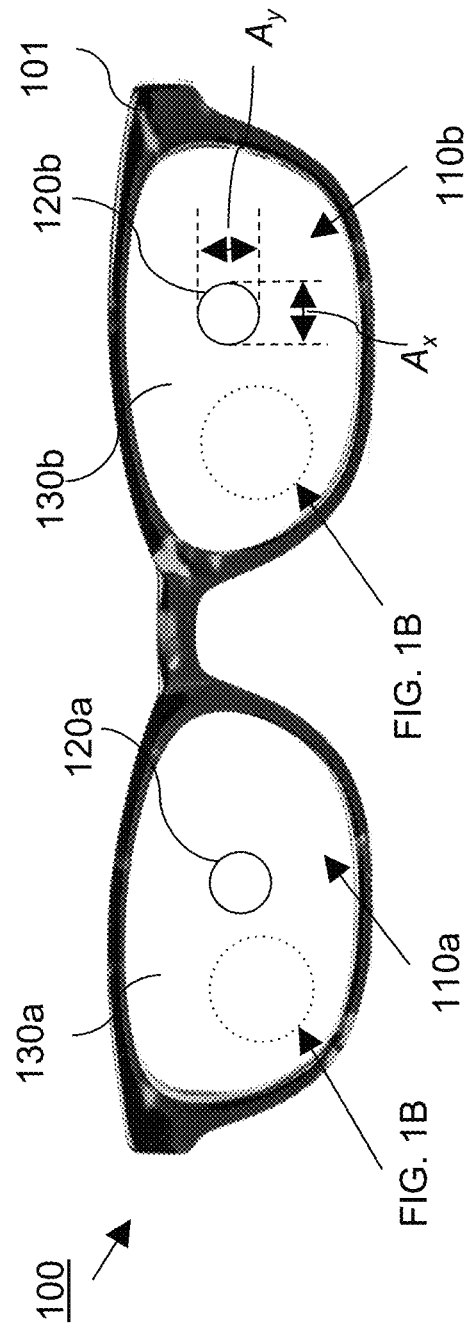
FIG. 1A shows a pair of eyeglasses containing ophthalmic lenses for treating myopia.

Referring to FIG. 1A, myopia-reducing eyeglasses 100 are disclosed which allow treatment of both eyes simultaneously without substantially compromising clear vision. Moreover, the eyeglasses are sufficiently robust and inconspicuous as to allow a wearer to engage in the same day-to-day activities without the eyeglasses failing and without feeling self-conscious about their appearance, which is especially desirable because the eyeglasses are typically used to arrest eye-lengthening in children.

Myopia-reducing eyeglasses 100 are composed of a pair of frames 101 and ophthalmic lenses 110a and 110b mounted in the frames. Generally, the ophthalmic lenses can be plano lenses, single vision lenses (e.g., with positive or negative power) or multivision lenses (e.g., bifocals or progressive lenses). Ophthalmic lenses 110a and 110b each have a clear aperture 120a and 120b, respectively, surrounded by reduced-contrast areas 130a and 130b, respectively. Clear apertures 120a and 120b are positioned to coincide with the wearer's on-axis viewing position, while reduced contrast areas 130a and 130b correspond to the wearer's peripheral vision. Referring also to FIG. 1B, reduced contrast areas 130a and 130b are composed of an array of dots 140, which reduce the contrast of an object in the wearer's peripheral vision by scattering light passing through those areas to the wearer's eye. In general, dots 140 can be provided by forming protrusions and/or recesses on one or both surfaces of each lens in areas 130a and 130b, and/or by forming scattering inclusions in the lens material itself in these areas.

The size and shape of the clear aperture may vary. Generally, the clear aperture provides the wearer with a viewing cone for which their visual acuity may be optimally corrected (e.g., to 20/15 or 20/20). In some embodiments, the aperture has a maximum dimension (in the x-y plane) in a range from about 0.2 mm (e.g., about 0.3 mm or more, about 0.4 mm or more, about 0.5 mm or more, about 0.6 mm or more, about 0.7 mm or more, about 0.8 mm or more, about 0.9 mm or more) to about 1.5 cm (e.g., about 1.4 cm or less, about 1.3 cm or less, about 1.2 cm or less, about 1.1 cm or less, about 1 cm or less). Where the aperture is circular, e.g., as depicted in FIG. 1A, this dimension corresponds to the circle's diameter (i.e., $A_x=A_y$), however non-circular (e.g., elliptical, polygonal, $A_x \cdot A_y$) apertures are also possible.

The clear aperture can subtend a solid angle of about 30 degrees or less (e.g., about 25 degrees or less, about 20 degrees or less, about 15 degrees or less, about 12 degrees or less, about 10 degrees or less, about 9 degrees or less, about 8 degrees or less, about 7 degrees or less, about 6 degrees or less, about 5 degrees or less, about 4 degrees or less, about 3 degrees or less) in the viewer's visual field. The solid angles subtended in the horizontal and vertical viewing planes may be the same or different.

In general, the dot patterns in reduced-contrast areas 130a and 130b can be selected based on a variety of design parameters to provide a desired degree of light scattering on the user's retina. Generally, these design parameters include the dot density, their size and shape, and their refractive index, for example, and are discussed in more detail below. Ideally, the dot patterns are selected to provide high visual acuity on the fovea and reduced image contrast on other parts of the retina with sufficiently low discomfort to the wearer to allow for extended, continuous wear. For instance, it can be desirable for children to be comfortable wearing the eyeglasses for most, if not all, of a day. Alternatively, or additionally, dot patterns can be designed for specific tasks, especially tasks which are believed to strongly promote eyelength growth, e.g., video gaming, reading or other wide angle, high contrast image exposure. For example, in such situations (e.g., where the user experiences high contrast in their peripheral vision and/or situations that do not require the wearer to move and to orient themselves using peripheral vision), the scattering intensity and scatter angle in the periphery can be increased, while considerations of consciousness and self-esteem may be less of a concern. This can lead to a higher efficiency in peripheral contrast reduction in such high contrast environment.

It is believed that reduced image contrast on the fovea of the user's eye is less efficient at controlling eye growth than reducing image contrast on other parts of the user's retina. Accordingly, the dot pattern can be tailored to reduce (e.g., minimize) light scattered into the user's fovea, while relatively more of the light on other parts of the retina is scattered light. The amount of scattered light on the fovea can be affected by the size of clear apertures 120a and 120b, respectively, but also by the nature of the dots, especially those closest to the clear apertures. In some embodiments, for example, the dots closest to the clear apertures can be designed for less efficient light scattering than those further away. Alternatively, or additionally, in some embodiments dots closest to the clear apertures can be designed for smaller angle forward scattering that those further from the aperture.

In certain embodiments, dots can be designed to deliver reduced narrow angle scattering and increased wide angle scattering to create even light distribution on retina/low contrast signal, while preserving acuity through geometry of scattering centers. For example, the dots can be designed to generate significant wide forward angle scattering (e.g., such as more than 10%, 20% or more, 30% or more, 40% or more, 50% or more, deflected by more than 2.5 deg.). Narrow angle forward scattering, i.e., within 2.5 deg., can be kept relatively low (e.g., 50% or less, 40% or less, 30% or less, 20% or less).

In general, a variety of different metrics can be used to evaluate the performance of dot patterns in order to optimize them for use in myopia reducing eye-glasses. For example, dot patterns can be optimized empirically, e.g., based on physical measurements of lenses with different dot patterns. For example, light scattering can be characterized based on haze measurements, such as international test standards for haze (e.g., ASTM D1003 and BS EN ISO 13468). Conventional hazemeters can be used, e.g., a BYK-Gardner haze meter (such as the Haze-Gard Plus instrument) that measures how much light is totally transmitted through a lens, the amount of light transmitted undisturbed (e.g., within 0.5 deg.), how much is deflected more than 2.5 deg., and clarity (amount within 2.5 deg.). Other equipment can also be used to characterize light scattering for purposes of empirically optimizing scattering patterns. For example, equipment which measures light diffusion by measuring light in annular ring around 2.5 deg. can be used (e.g., equipment from Hornell).

Alternatively, or additionally, dot patterns can be optimized by computer modelling software (e.g., Zemax or Code V).

In some embodiments, dot patterns can be designed based on optimization of a point spread function, which is a representation of an image of the scattering center on the retina. For example, the size, shape, and spacing of the scattering centers can be varied to evenly spread illumination of retina such that the retina outside of fovea is homogeneously blanketed with scattered light to reduce (e.g., minimize) contrast at this region of the retina.

Alternatively, or additionally, dot patterns can be designed based on optimization of a modulation transfer function, which refers to the spatial frequency response of the human visual system. For instance, the size, shape, and spacing of the scattering centers can be varied to smoothen attenuation of a range of spatial frequencies. Design parameters of the dot pattern can be varied in order to increase or decrease certain spatial frequencies as desired. Generally, the spatial frequencies of interest for vision are 18 cycles per deg. on the fine side, and 1.5 cycles per deg. on the course side. Dot patterns can be designed to provide increased signal at certain subsets of spatial frequencies within this range.

The aforementioned metrics can be used to evaluate dot patterns based on the size and/or shape of the dots, both of which can be varied as desired. For example, the dots can be substantially round (e.g., spherical), elongate (e.g., ellipsoidal), or irregularly-shaped. Generally, the protuberances should have a dimension (e.g., diameter, as depicted in FIG. 1B) that is sufficient large to scatter visible light, yet sufficiently small so as not to be resolved by the wearer during normal use. For example, the dots can have a dimension (as measured in the x-y plane) in a range from about 0.001 mm or more (e.g., about 0.005 mm or more, about 0.01 mm or more, about 0.015 mm or more, about 0.02 mm or more, about 0.025 mm or more, about 0.03 mm or more, about 0.035 mm or more, about 0.04 mm or more, about 0.045 mm or more, about 0.05 mm or more, about 0.055 mm or more, about 0.06 mm or more, about 0.07 mm or more, about 0.08 mm or more, about 0.09 mm or more, about 0.1 mm) to about 1 mm or less (e.g., about 0.9 mm or less, about 0.8 mm or less, about 0.7 mm or less, about 0.6 mm or less, about 0.5 mm or less, about 0.4 mm or less, about 0.3 mm or less, about 0.2 mm or less, about 0.1 mm).

Note that for smaller dots, e.g., having a dimension that is comparable to the wavelength of light (e.g., 0.001 mm to about 0.05 mm), the light scattering may be considered Raleigh or Mie scattering. For larger protuberances, e.g., about 0.1 mm or more, light scattering may be due to geometric scattering.

In general, the dimension of the dots may be the same across each lens or may vary. For example, the dimension may increase or decrease as a function of the location of the protuberance, e.g., as measured from the clear aperture and/or as a function of distance from an edge of the lens. In some embodiments, the protuberance dimensions vary monotonically as the distance from the center of the lens increases (e.g., monotonically increase or monotonically decrease). In some cases, monotonic increase/decrease in dimension includes varying the diameter of the protuberances linearly as a function of the distance from the center of the lens.

The dots shown in FIG. 1B are arranged on a square grid, spaced apart by a uniform amount in each direction. This is shown by $D_y$ in the y-direction and $D_x$ in the x-direction. In general, the dots are spaced so that, collectively, they provide sufficient contrast reduction in the viewer's periphery for myopia reduction. Typically, smaller dot spacing will result in greater contrast reduction (provided adjacent dots do not overlap or merge). In general, $D_x$ and $D_y$ are in a range from about 0.05 mm (e.g., about 0.1 mm or more, about 0.15 mm or more, about 0.2 mm or more, about 0.25 mm or more, about 0.3 mm or more, about 0.35 mm or more, about 0.4 mm or more, about 0.45 mm or more, about 0.5 mm or more, about 0.55 mm or more, about 0.6 mm or more, about 0.65 mm or more, about 0.7 mm or more, about 0.75 mm or more) to about 2 mm (e.g., about 1.9 mm or less, about 1.8 mm or less, about 1.7 mm or less, about 1.6 mm or less, about 1.5 mm or less, about 1.4 mm or less, about 1.3 mm or less, about 1.2 mm or less, about 1.1 mm or less, about 1 mm or less, about 0.9 mm or less, about 0.8 mm or less). As an example, dot spacing can be 0.55 mm, 0.365 mm, or 0.240 mm.

While the dots shown in FIG. 1B are arranged with equal spacing in the x- and y-directions, more generally spacing in each direction may be different. Furthermore, protuberances may be arrayed in grids that are not square. For example, hexagonal grids may be used. Non-regular arrays are also possible, e.g., random or semi-random dot placement may be used. In the case of a random pattern dimensions given would be the average separation of the dots in x- and y-directions.

In general, the coverage of a lens by dots can vary as desired. Here, coverage refers to the proportion of the lens's total area, as projected onto the x-y plane that corresponds to a dot. Typically, a lower dot coverage will yield lower scattering than higher dot coverage (assuming individual dots are discrete, i.e., they do not merger to form larger dots). Dot coverage can vary from 10% or more to about 75%. For example, dot coverage can be 15% or more, 20% or more, 25% or more, 30% or more, 35% of more, 40% or more, 45% or more, such as 50% or 55%). Dot coverage can be selected according to a comfort level of a user, e.g., to provide a level of peripheral vision sufficiently comfortable that the wearer will voluntarily wear the eyeglasses for extended periods (e.g., all day).

While the dots are depicted as have circular footprints in FIG. 1B, more generally the dots can have other shapes. For example, the dots can be elongated in one direction (e.g., in the x-direction or y-direction), such as in the case of elliptical dots. In some embodiments, the dots are random on shape.

It is believed that light from a scene that is incident on the lenses in reduced contrast areas 130a and 130b between the dots contributes to an image of the scene on the user's retina, while light from the scene incident on the dots does not. Moreover, the light incident on the dots is still transmitted to the retina, so has the effect of reducing image contrast without substantially reducing light intensity at the retina. Accordingly, it is believed that the amount of contrast reduction in the user's peripheral field of view is correlated to (e.g., is approximately proportional to) the proportion of the surface area of the reduced-contrast areas covered by the dots. Generally, dots occupy at least 10% (e.g., 20% or more, 30% or more, 40% or more, 50% or more, such as 90% or less, 80% or less, 70% or less, 60% or less) of the area (as measured in the x-y plane) of reduced contrast area 130a and 130b.

In general, the dot pattern reduces the contrast of images of objects in the wearer's peripheral vision without significantly degrading the viewer's visual acuity in this region. Here, peripheral vision refers to the field of vision outside of the field of the clear aperture. Image contrast in these regions can be reduced by 40% or more (e.g., 45% or more, 50% or more, 60% or more, 70% or, more, 80% or more) relative to an image contrast viewed using the clear aperture of the lens as determined. Contrast reduction may be set according to the needs of each individual case. It is believed that a typical contrast reduction would be in a range from about 50% to 55%. Contrast reductions of lower than 50% may be used for very mild cases, while subjects who are more predisposed might need a higher than 55% contrast reduction. Peripheral visual acuity can be corrected to 20/30 or better (e.g., 20/25 or better, 20/20 or better) as determined by subjective refraction, while still achieving meaningful contrast reduction.

Contrast, here, refers to the difference in luminance between two objects within the same field of view. Accordingly, contrast reduction refers to a change in this difference.

Contrast and contrast reduction may be measured in a variety of ways. In some embodiments, contrast can be measured based on a brightness difference between different portions of a standard pattern, such as a checkerboard of black and white squares, obtained through the clear aperture and dot pattern of the lens under controlled conditions.

Alternatively, or additionally, contrast reduction may be determined based on the optical transfer function (OTF) of the lens (see, e.g., http://www.montana.edu/jshaw/documents/18%20EELE582_S15_OTFMTF.pdf). For an OTF, contrast is specified for transmission of stimuli in which light and dark regions are sinusoidally modulated at different "spatial frequencies." These stimuli look like alternating light and dark bars with the spacing between bars varying over a range. For all optical systems the transmission of contrast is lowest for the sinusoidally varying stimuli having the highest spatial frequencies. The relationship describing the transmission of contrast for all spatial frequencies is the OTF. The OTF can be obtained by taking the Fourier transform of the point spread function. The point spread function can be obtained by imaging a point source of light through the lens on to a detector array and determining how light from a point is distributed across the detector.

In the event of conflicting measurements, the OTF is technique is preferred. In some embodiments, contrast may be estimated based on the ratio of the area of the lens covered by dots compared to the area of the clear aperture. In this approximation, it is assumed that all the light that hits the dots becomes uniformly dispersed across the entire retinal area, which reduce the amount of light available in lighter areas of an image and this adds light to darker areas. Accordingly, contrast reduction may be calculated based on light transmission measurements made through the clear aperture and dot pattern of a lens.

Generally, ophthalmic lenses 110a and 110b can be clear or tinted. That is, the lenses may be optically transparent to all visible wavelengths, appearing clear and/or colorless, or may include a spectral filter, appearing colored. For example, ophthalmic lenses may include a filter that reduces the amount of red light transmitted to the wearer. It is believed that excessive stimulation of L cones in a person's eye (especially in children), may result in non-optimal eye lengthening and myopia. Accordingly, spectrally filtering red light using the ophthalmic lenses may further reduce myopia in a wearer.

Spectral filtering may be provided by applying a film to a surface of the lenses. Films may be applied by physically depositing material onto a lens surface, coating a layer of material on the surface, or laminating a preformed film onto the surface. Suitable materials include absorptive filter materials (e.g., dyes) or multilayer films, providing interference filtering. In some embodiments, spectral filtering may be provided by including a filtering material in the lens material itself and/or including a filtering material in the material used to form the protuberance.

Figure 2:
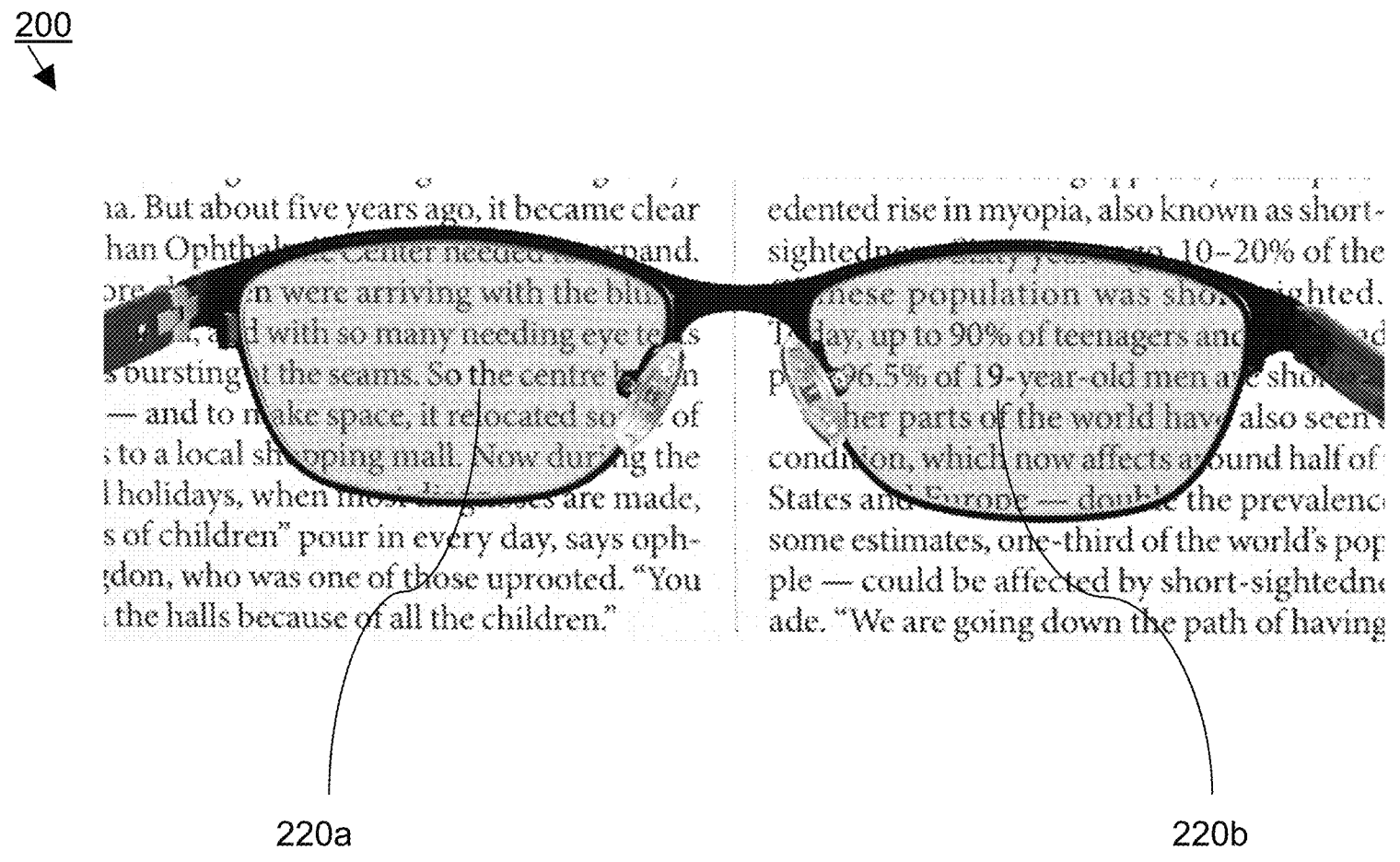

Referring to FIG. 2, the effect of spectral filtering and contrast reduction from the dot pattern is shown by viewing black text on a white background using eyeglasses 210. The white background to the text takes on a green appearance due to the filtering of red wavelengths from by the eyeglasses. Image contrast is unaffected at clear apertures 220a and 220b, but is reduced elsewhere in the viewer's visual frame.

As noted above, in general, the dots can be provided as protuberances and/or recesses on one or both surfaces of each lens, and/or as scattering inclusions in the lens material itself. In some embodiments, the dots can be formed by arrays of protuberances on a surface (e.g., the back surface or the front surface) of each of lenses 110a and 110b.

The protuberances can be formed from an optically transparent material having a similar refractive index to the underlying lens, which is 1.60 for polycarbonate. For example, in embodiments where the lenses are formed from polycarbonate, the protuberances can be formed from a polymer having a similar refractive index to the PC, such as from light-activated polyurethane or epoxy based plastics. In addition to PC, the lenses themselves can also be made from allyl diglycol carbonate plastic, a urethane-based monomer or other impact resistant monomers. Alternatively, lenses could be made from one of the more-dense high-refractive index plastics with an index of refraction greater than 1.60. In some embodiments, the lenses are made from optically transparent materials with lower index of refraction (e.g., CR39 is at 1.50, Trivex is at 1.53).

Figure 3A:
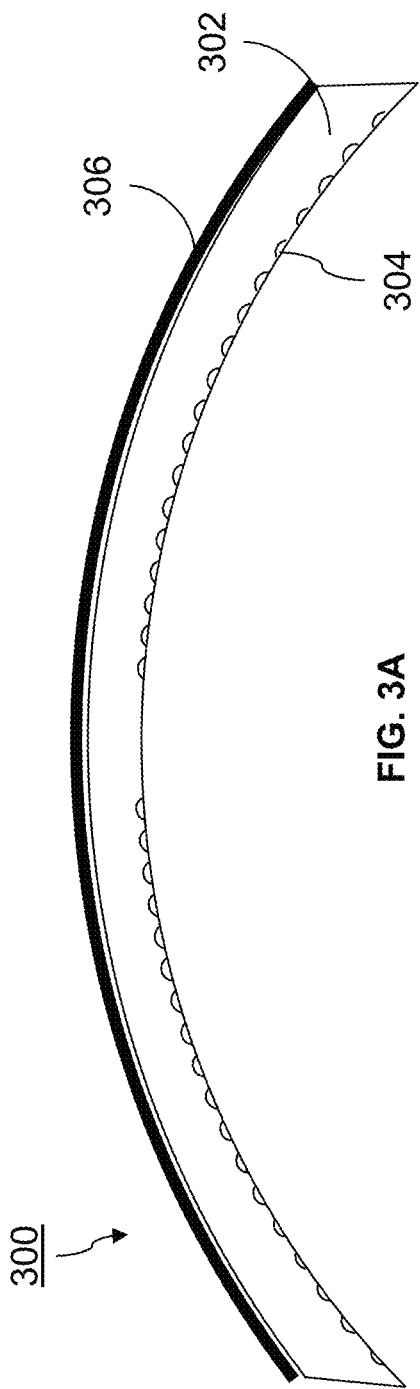
FIG. 3A shows a cross-sectional view of an exemplary lens material removed from a surface of the lens.

Surface dot patterns can also be formed by generating recesses in one or both surfaces of a lens. For example, referring to FIG. 3A, a lens 300 includes a dot pattern formed from recesses 304 formed on a surface of the lens body 302. In this example, a negatively powered meniscus lens is depicted. More generally, positive power or unpowered lenses can be used too. Recesses 304 can have dimensions and/or spacing similar to those of the protuberances described above. Recesses 304 can be formed using a variety of techniques, such as etching (e.g., physical etching or chemical etching) or ablating material from the lens surface (e.g., using laser radiation or a molecular or ion beam). In some embodiments, recesses are formed when molding the lens. The recesses can, in some cases, each correspond to of a region of the lens surface where sufficient material is removed to roughen the surface so that the lens surface scatters, rather than refracts, incident light.

Lens 300 also includes an optical coating 306 on the surface of lens body 302 opposite recesses 304. Optical coating 306 can perform one or more functions, such as antireflection, spectral filtering (e.g., UV filtering), and or a protective hardcoat.

In some embodiments, contrast reduction is produced by other diffusing structures, such as a roughened surface. Holographic diffusers or ground glass diffusers may be used. In some embodiments, a diffuser may be provided by a film that is laminated onto a surface of the lens.

Figure 3B:
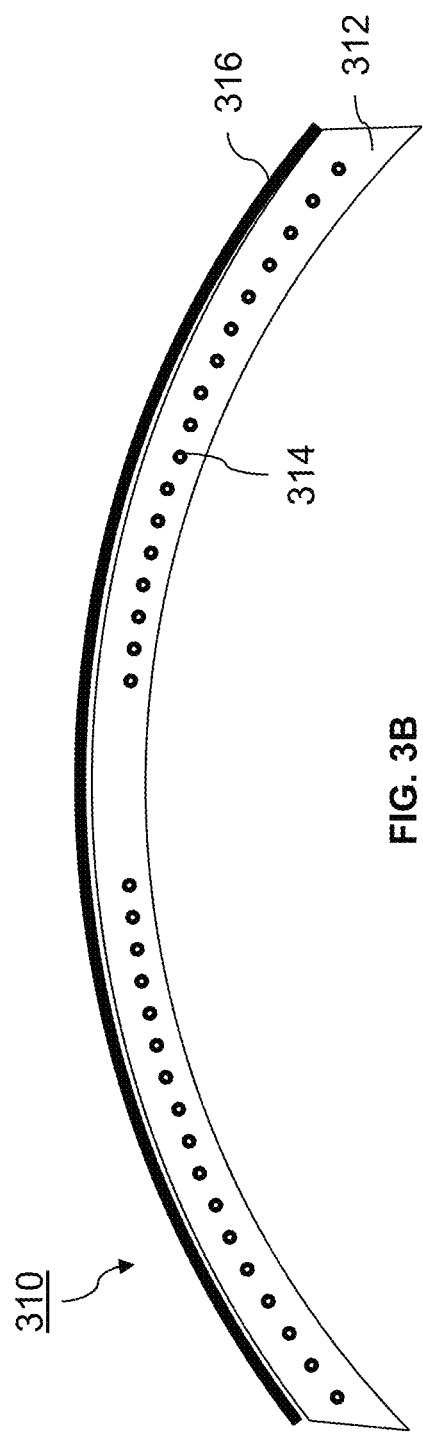
FIG. 3B shows a cross-sectional view of an exemplary lens with scattering inclusions between opposing surfaces of the lens.

Referring to FIG. 3B, a cross-sectional view of another lens 310 is shown. This lens includes a lens body 312 that includes embedded scattering centers 314. Lens 310 also includes an optical coating 316 on one of the lens body's surfaces. Optical coatings on both surfaces are also possible. Scattering centers are generally formed from a material that has a refractive index mismatch from the bulk lens material. For example, transparent beads of appropriate size can be dispersed in the lens material when the lens is molded, where the refractive index of the bead material and bulk lens material differ. The clear aperture is formed from bulk lens material only.

In some embodiments, embedded scattering centers 314 can be formed using a process that selectively induces a refractive index change in the lens bulk material. For example, exposure to a laser beam can cause a local change in the refractive index of bulk lens material, e.g., through a photochemical and/or photothermal interaction. Exemplary laser exposure methods that can be used to localize the dot pattern as described in more detail below.

Generally, the refractive index mismatch between the lens material and the dot material affects the amount of light scattered at each protuberance, e.g., as calculated using a point spread function. Typically, the larger the refractive index mismatch between the materials, the more incident light will be scattered. Accordingly, refractive index mismatch can be used as a design parameter with which to optimize the scattering properties of the dots.

In some embodiments, the protuberance material is selected to have a refractive index that is within 0.1 (e.g., within 0.09 or less, 0.08 or less, 0.07 or less, 0.06 or less, 0.05 or less, 0.04 or less, 0.03 or less, 0.02 or less, 0.01 or less, 0.005 or less, 0.002 or less, 0.001 or less) of the refractive index of the lens material (e.g., as measured at one or more wavelengths in the visible light range).

In certain embodiments, larger refractive index mismatches (e.g., more than 0.1) are possible. For example, the protuberance material can be selected to have a refractive index that differs from the refractive index of the lens material by 0.15 or more (e.g., 0.2 or more, 0.25 or more, 0.3 or more, 0.35 or more, such as up to about 0.4).

In general, the refractive index of each dot can be the same or different. For example, where the dots are each formed from the same material, each one can have the same refractive index. Alternatively, in some embodiments, the refractive index can vary from dot-to-dot or between different groups of dots. For example, in certain implementations, the refractive index mismatch between the dots and the lens bulk material can increase as the radial distance from the lens axis increases in order to increasing the amount of light scattering from each dot as the radial distance from the lens axis increases.

In some instances, dots can be formed from materials that absorb at least some light incident thereon, such as dyes. The materials can be selected to absorb broadband visible light, or absorb light only at certain wavelengths (e.g., absorb a short wavelength component or long wavelength component). It is believed that light absorptive materials can help reduce glare and/or provide another design parameter for shaping the point spread function of the dots. In some embodiments, exposure to radiation can change the lens material from transparent to absorptive at certain wavelengths. For instance, the exposing radiation can burn the lens material in order to form light absorbing centers in the lens material or on its surface.

As noted previously, in general, the size, spacing, and arrangement of the dot pattern can vary. In some embodiments, the dot pattern features a gradient in, e.g., dot size and/or spacing. Dot patterns can feature a gradient in scattering efficiency of the dots (e.g., due to a gradient in the refractive index mismatch and/or shape of each dot). Graded dot patterns can reduce the conspicuity of the pattern. For example, a graded transition from the clear portions of the lens to the scattering portion can be less conspicuous than a sharp transition.

In some embodiments, a lens can feature different zones in which the dot pattern varies from zone-to-zone. For example, referring to FIGS. 4A and 4B, a lens 400 includes a clear aperture 410, a transition zone 420, and a scattering zone 430. Clear aperture 410 has a radius $R_{410}$ and transition zone 420 is an annular region surrounding the clear aperture having an inner radius $R_{410}$ and an outer radius $R_{420}$. The remainder of the lens area forms scattering zone 430.

Transition zone 420 features a dot pattern that scatters incident light less than the dot pattern in scattering zone 430, providing a transition in the scattering properties of the lens from the clear aperture to the scattering zone. Such a transition may be advantageous in that it reduces scattering into the fovea compared to scattering that would be provided if the scattering zone extended to the clear aperture. A further advantage is that the transition zone may reduce the visibility of the dot pattern to the user, providing a more comfortable wearing experience. This can be particularly important for children, where the likelihood that a child will regularly wear eyeglasses featuring such lenses for extended periods depends on the child's comfort level.

Generally, the dot pattern in transition zone 420 can vary. In some embodiments, the transition zone features a uniform dot pattern in which the dots have the same shape and size and are uniformly spaced. Alternatively, in certain embodiments, the dot pattern in the transition zone can feature varying dot density, spacing, and/or size. For example, the dot pattern can be selected to provide the weakest scattering closest to the clear aperture, with monotonically increasing scattering at increasing radial distances from $R_{410}$ to $R_{420}$. For example, in some embodiments, the dot density increases monotonically (e.g., linearly) from $R_{410}$ to $R_{420}$. By way of example, the dot diameter can increase linearly from a first value (e.g., 0.05 mm) to a second value (e.g., 0.17 mm) as the radial distance from the lens axis increases from $R_{410}$ to $R_{420}$. Alternatively, or in addition, the dot spacing can decrease monotonically (e.g., linearly) from $R_{410}$ to $R_{420}$.

Typically, $R_{410}$ is in a range from about 1 mm to about 3 mm (e.g., 1.0 mm to 1.1 mm, 1.1 mm to 1.2 mm, 1.2 mm to 1.3 mm, 1.3 mm to 1.4 mm, 1.4 mm to 1.5 mm, 1.5 mm to 1.6 mm, 1.6 mm to 1.7 mm, 1.7 mm to 1.8 mm, 1.8 mm to 1.9 mm, 1.9 mm to 2.0 mm, 2.0 mm to 2.1 mm, 2.1 mm to 2.2 mm, 2.2 mm to 2.3 mm, 2.3 mm to 2.4 mm, 2.4 mm to 2.5 mm, 2.5 mm to 2.6 mm, 2.6 mm to 2.7 mm, 2.7 mm to 2.8 mm, 2.8 mm to 2.9 mm, 2.9 mm to 3.0 mm).

$R_{420}$ can be in a range from about 2 mm to about 6 mm (e.g., 2.0 mm to 2.2 mm, 2.2 mm to 2.4 mm, 2.4 mm to 2.6 mm, 2.6 mm to 2.8 mm, 2.8 mm to 3.0 mm, 3.0 mm to 3.2 mm, 3.2 mm to 3.4 mm, 3.4 mm to 3.6 mm, 3.6 mm to 3.8 mm, 3.8 mm to 4.0 mm, 4.0 mm to 4.2 mm, 4.2 mm to 4.4 mm, 4.4 mm to 4.6 mm, 4.6 mm to 4.8 mm, 4.8 mm to 5.0 mm, 5.0 mm to 5.2 mm, 5.2 mm to 5.4 mm, 5.4 mm to 5.6 mm, 5.6 mm to 5.8 mm, 5.8 mm to 6.0 mm).

In some embodiments, the dot pattern includes randomly displacing dots with respect to a regular array. Introducing random displacements can reduce optical effects associated with regularly spaced scattering centers, such as starburst-like glare. See, e.g., https://www.slrlounge.com/diffraction-aperture-and-starburst-effects/which illustrates the starburst effect as it relates to photography. Accordingly, including random displacements in dot patterns can provide the user with a more comfortable experience compared with similar dot patterns in which the scattering centers are uniformly spaced. Alternatively, or additionally, randomization of the dot pattern can reduce the optical effects (e.g., diffractive or interference effects) that manifest in reflected light, reducing the noticeability of the dot patterns to observers.

Figures 4A, 4B, 4C:
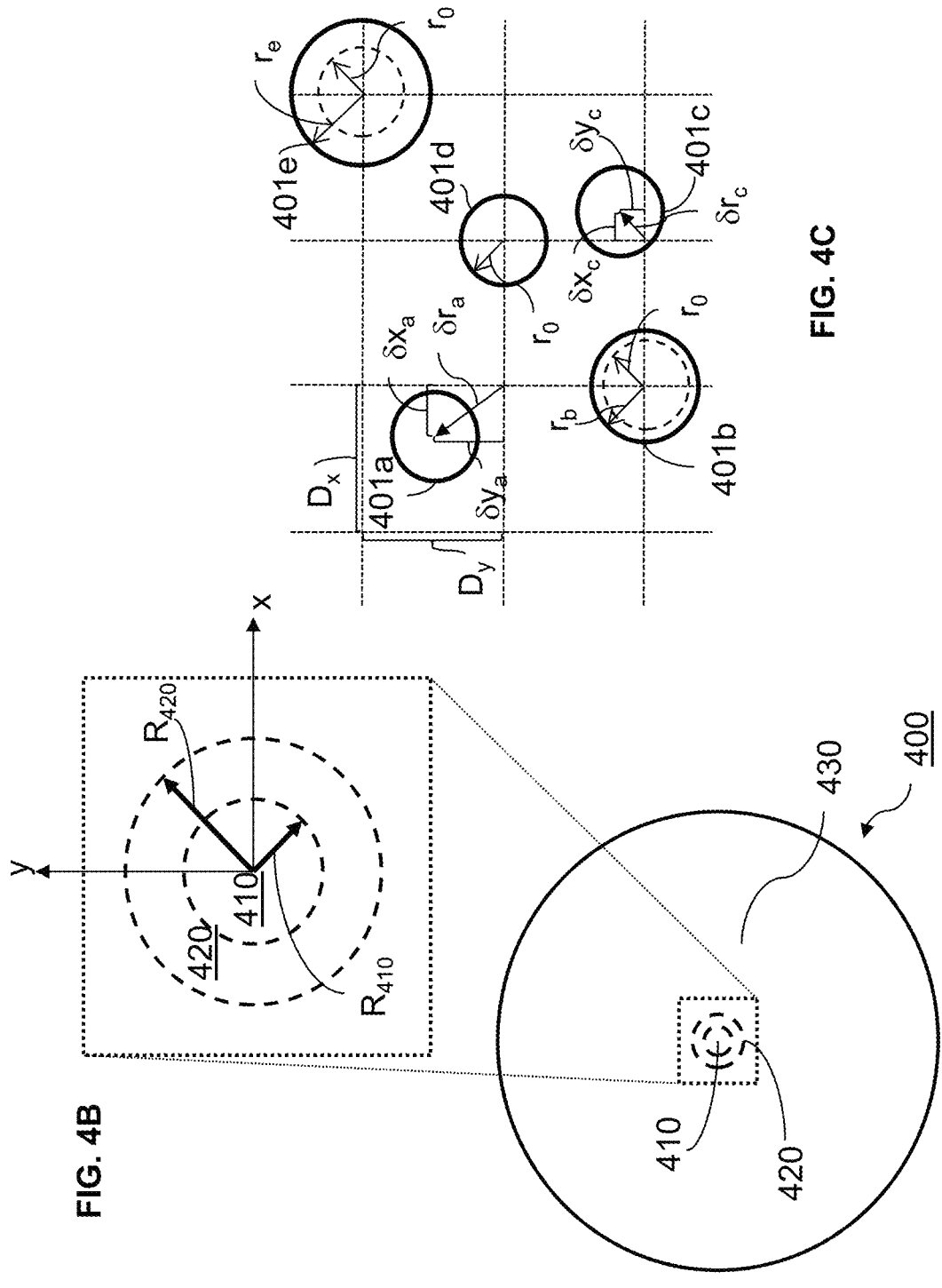
FIGS. 4A and 4B show a lens blank with a dot pattern that has a transition zone between a clear aperture and the dot pattern.
FIG. 4C shows dots with a random displacement from uniform spacing.
Figure 5A:
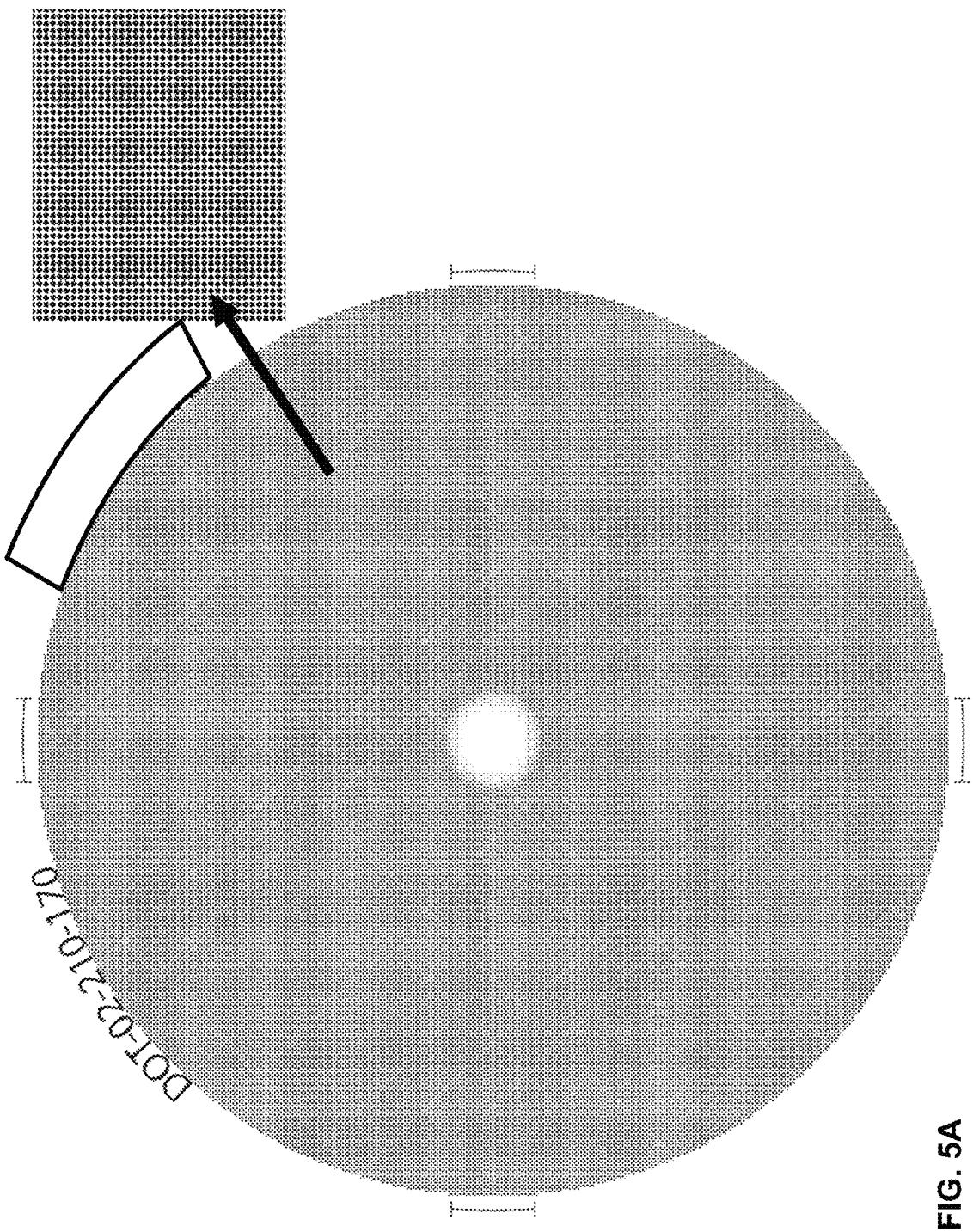
FIG. 5A shows an exemplary dot pattern with a transition zone and uniformly spaced dots.
Figure 5B:
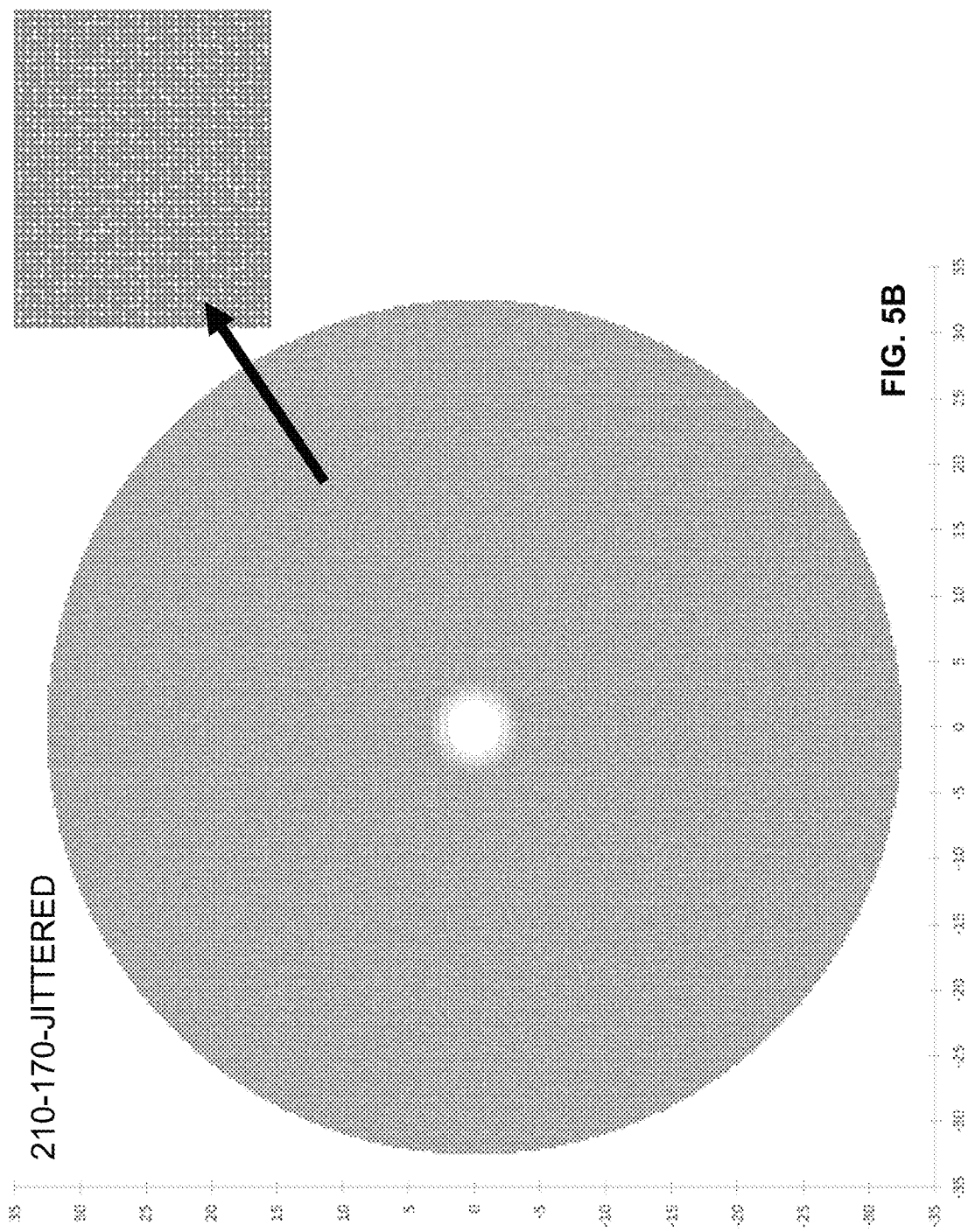
FIG. 5B shows an exemplary dot pattern with a transition zone and dots with a random displacement from uniform spacing.
Figure 5C:
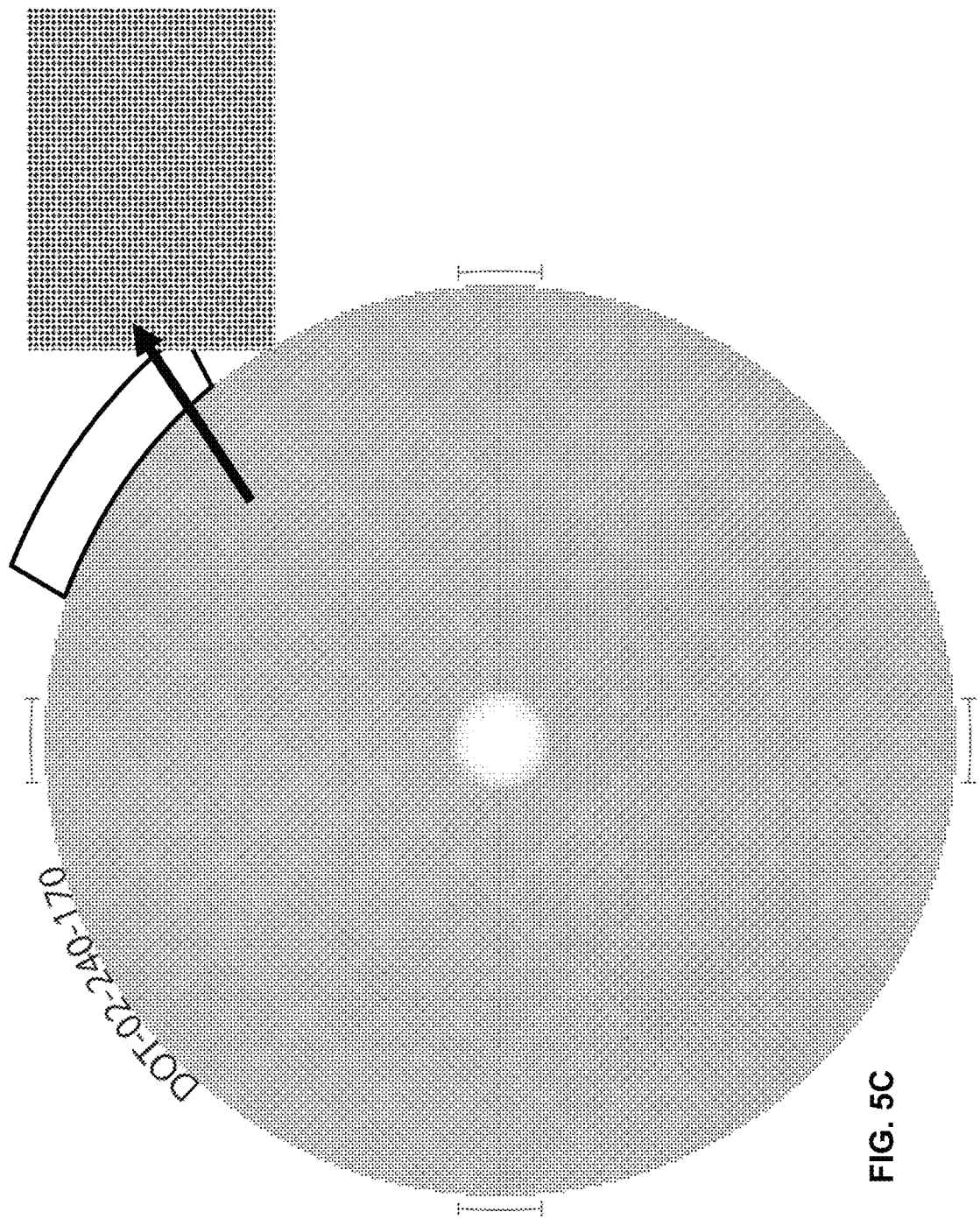
FIG. 5C shows another exemplary dot pattern with a transition zone and uniformly spaced dots.
Figure 5D:
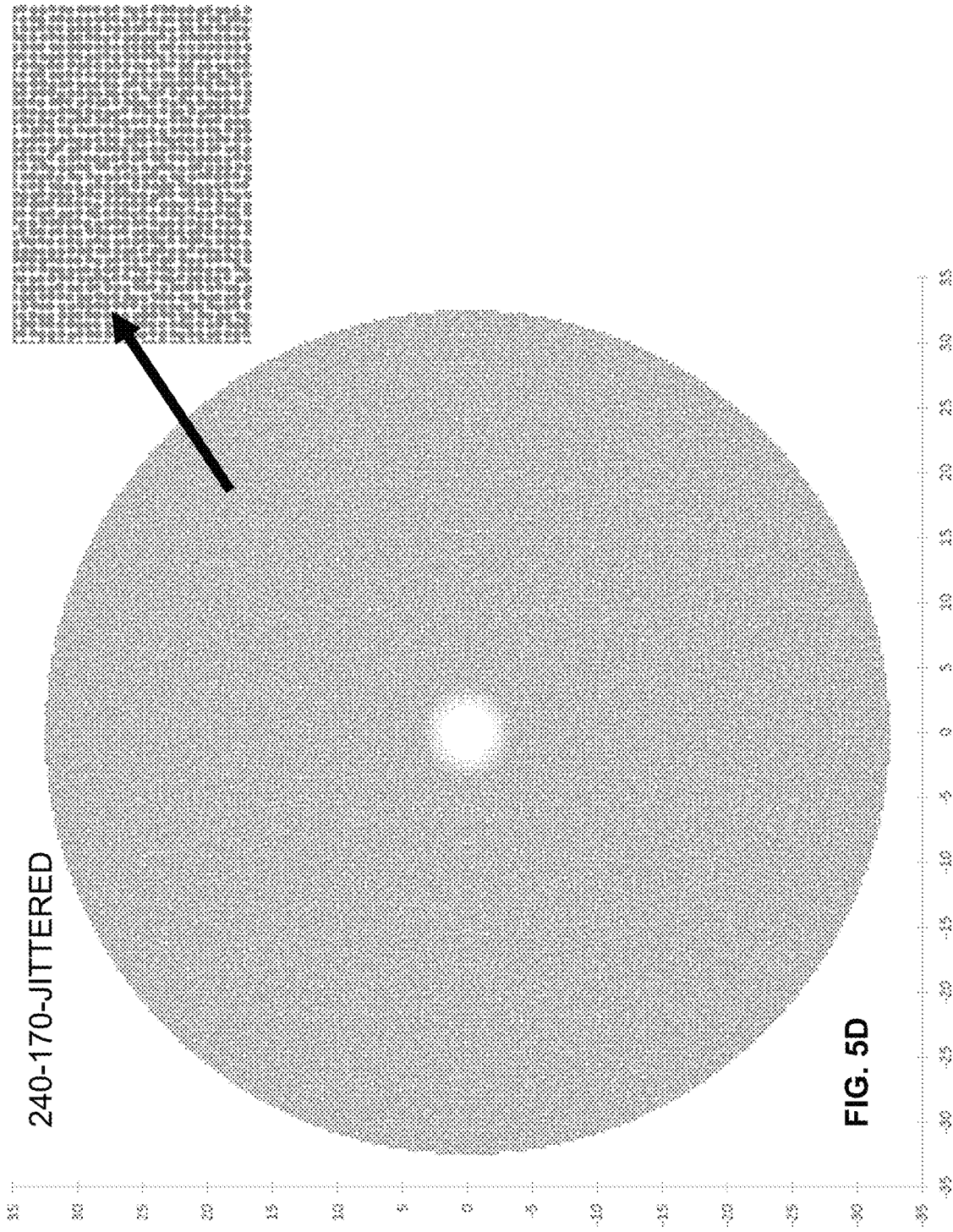
FIG. 5D shows another exemplary dot pattern with a transition zone and dots with a random displacement from uniform spacing.
Figure 5E:
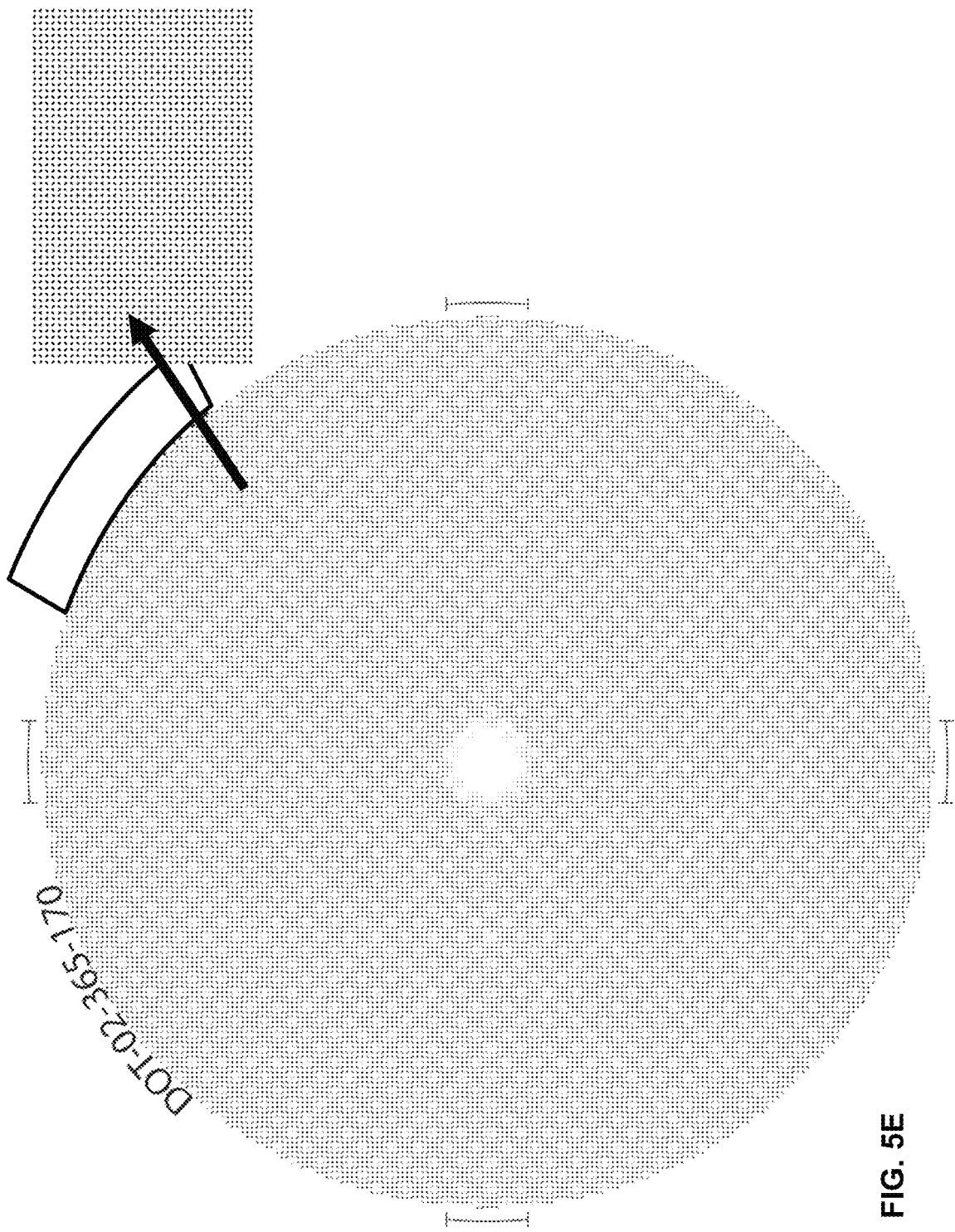
FIG. 5E shows a further exemplary dot pattern with a transition zone and uniformly spaced dots.
Figure 5F:
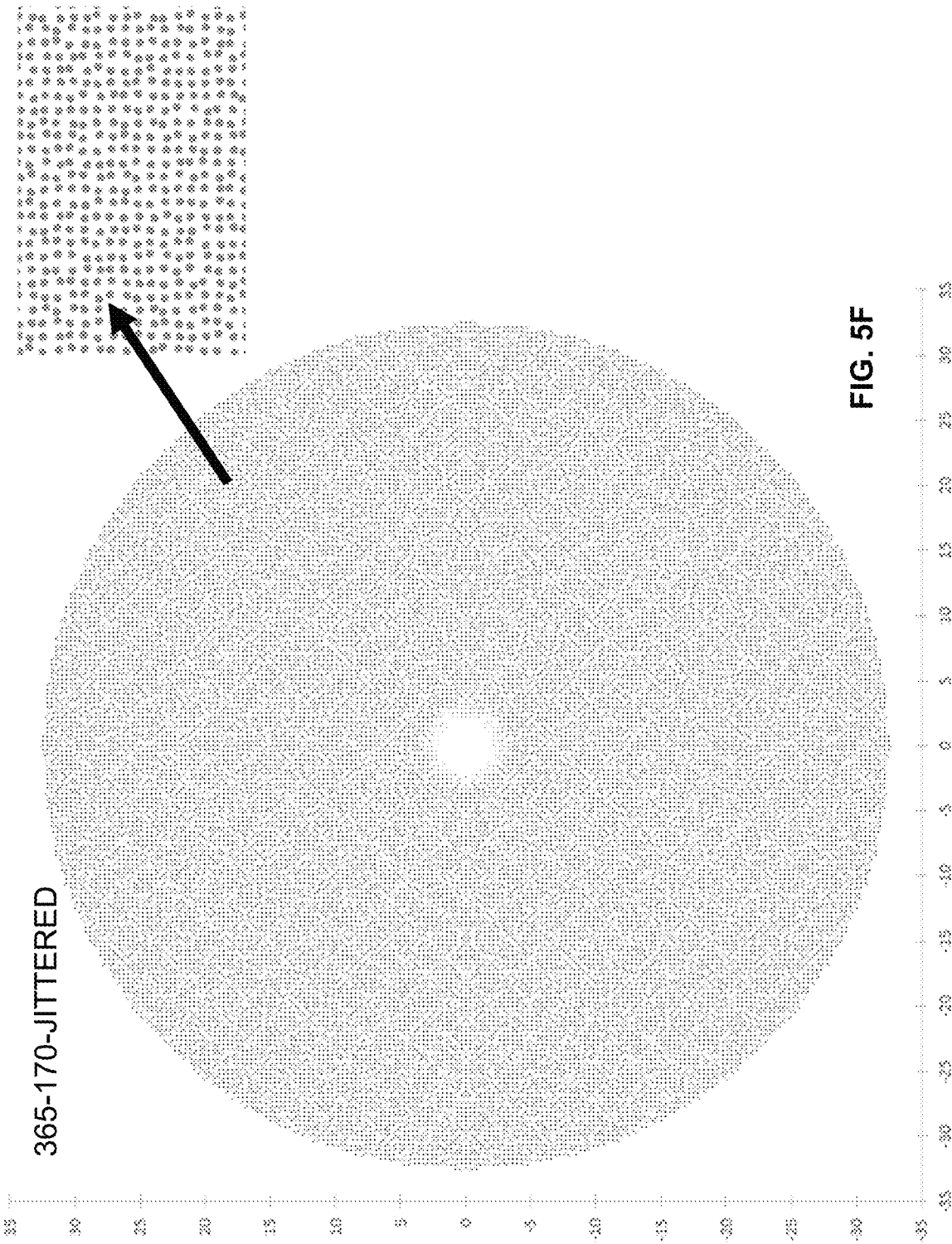
FIG. 5F shows a further exemplary dot pattern with a transition zone and dots with a random displacement from uniform spacing.

Random displacements are illustrated in FIG. 4C, which shows dots 401a-401e positioned with respect to an array lattice in which adjacent lattice sites are spaced a distance $D_x$ from each other in the x-direction and a distance $D_y$ from each other in the y-direction. As illustrated, $D_x=D_y$, however, more generally, the vertical and horizontal lattice spacing can be different.

For each dot, $\delta x = A_x \cdot D_x \cdot RN[0,1]$ and $\delta y = A_y \cdot D_y \cdot RN[0,1]$ where $A_x$ and $A_y$ are jitter amplitudes between 0 and 1 in the x- and y-directions, respectively, which may be the same or different. $RN[0,1]$ is a random number between 0 and 1.

Dot size can also vary randomly, which can reduce optical effects associated with an array of uniformly sized dots, such as glare. For example, as illustrated in FIG. 4C, the radial dimension of each dot can vary from a nominal dot radius, $r_0$. As illustrated, dot 401d has nominal dot radius $r_0$, while dots 401b and 401e have radii $r_b$ and $r_e$, respectively that are both larger than $r_0$ and $r_b \neq r_e$. Dot radius can be set according to a formula $r_i = r_0 + \Delta r$, where $\Delta r = A_r \cdot r_0 \cdot RN[0,1]$, in which i refers to the i-th dot and $A_r$ is the dot radius jitter amplitude which is set to a value between 0 and 1.

More generally, while the example above refers to dot radius of a nominally circular dot, jitter can be applied to other dot-size parameters depending on the application. For example, jitter can be applied to dot volume or other dot dimensions (e.g., x-dimension, y-dimension).

In some embodiments, dot patterns can include both random jitter in dot placement and random jitter in dot size.

Exemplary dot patterns featuring a transition zone are shown in FIGS. 5A-5F. The patterns in FIGS. 5A, 5C, and 5E feature uniformly spaced dots in the scattering zone. The patterns in FIGS. 5B, 5D, and 5F feature dots that are randomly displaced from uniform spacing. The units for both the horizontal and vertical axes are mm. Each of FIGS. 5A-5F includes an inset showing a magnified view of the corresponding dot pattern. The parameters characterizing the dot patterns are provided in the table below.

| FIG. | Dot Pattern | Clear Aperture radius | Transition Zone radius | Scattering Zone | | |
|---|---|---|---|---|---|---|
| | | | | Dot lattice spacing | Dot dimension | Jitter amplitude |
| 5A | DOT-02-210-170 | 2 mm | 3.5 mm | 0.21 mm | 0.17 mm | 0 |
| 5B | 210-170-JITTERED | 2 mm | 3.5 mm | 0.21 mm | 0.17 mm | 0.1 |
| 5C | DOT-02-240-170 | 2 mm | 3.5 mm | 0.24 mm | 0.17 mm | 0 |
| 5D | 240-170-JITTERED | 2 mm | 3.5 mm | 0.24 mm | 0.17 mm | 0.15 |
| 5E | DOT-02-365-170 | 2 mm | 3.5 mm | 0.365 mm | 0.17 mm | 0 |
| 5F | 365-170-JITTERED | 2 mm | 3.5 mm | 0.365 mm | 0.17 mm | 0.2 |

In some embodiments, the dot pattern features a gradient in, e.g., dot size and/or spacing. Dot patterns can feature a gradient in scattering efficiency of the dots (e.g., due to a gradient in the refractive index mismatch and/or shape of each dot). Graded dot patterns can reduce the conspicuity of the pattern. For example, a graded transition from the clear portions of the lens to the scattering portion can be less conspicuous than a sharp transition.

Figure 6A:
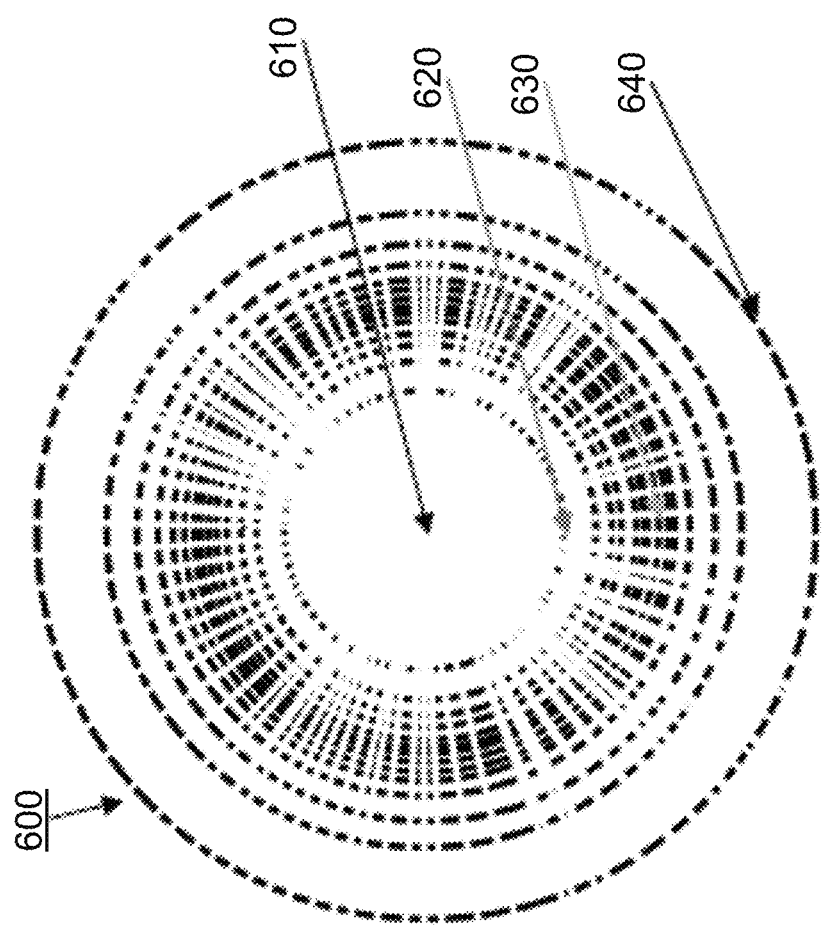
FIG. 6A shows an exemplary lens having a graded dot pattern with different spacing between adjacent dots.
Figure 6B:
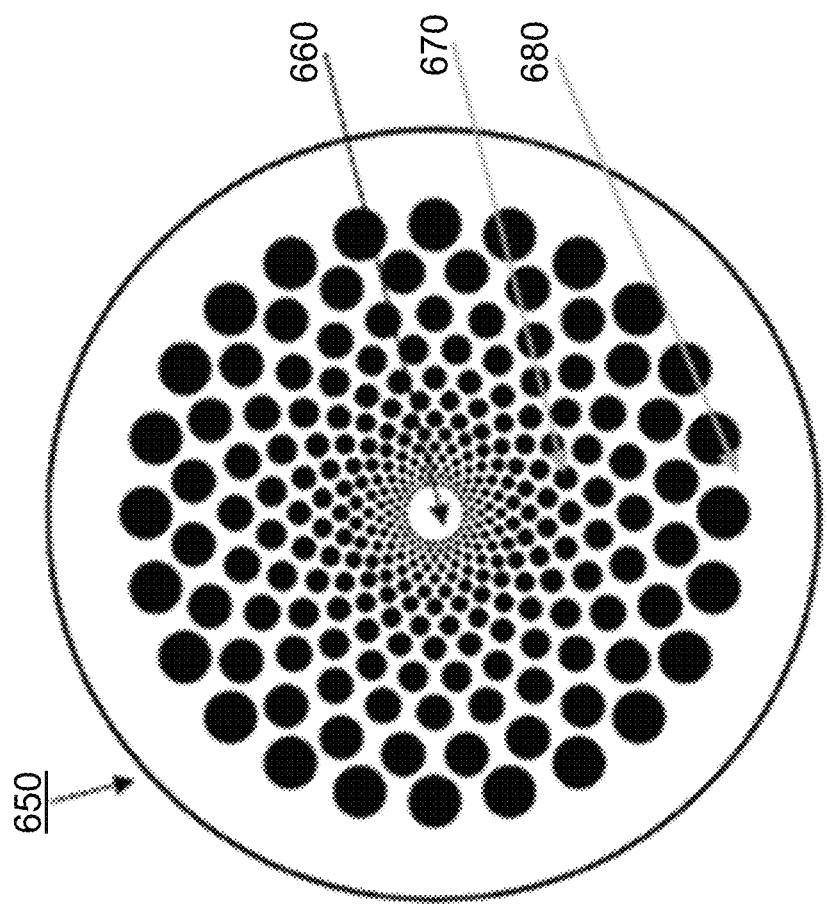
FIG. 6B shows an exemplary lens having a graded dot pattern with varying dot size.

Referring to FIGS. 6A and 6B, exemplary graded dot patterns are shown.

Specifically, FIG. 6A shows a graded dot pattern 600 with different spacing between adjacent dots. Clear aperture 610 transitions into low-density region 620. In region 620, distance between adjacent dots is relatively large, thus rendering a low density of dots in region 620. Low-density region 620 then transitions into high-density region 530, where the spacing between adjacent dots is small, thus rendering a high density of dots. High-density region 630 then transitions into low-density region 640, where the spacing between adjacent dots is again increased. As a result, due to the graded transition from clear aperture 610 to the outer edge of the lens, the graded dot pattern can be less conspicuous compared to a transition to a higher density, uniform dot pattern.

Dot density can be controlled not only by the spacing between adjacent dots, but also by dot size. Referring to FIG. 6B, for example, a dot pattern 650 features dots close to clear aperture 660 that have smaller size compared to dots closer to an edge 680 of the dot pattern.

In another example, a lens can have a graded dot pattern with both varying dot size and dot-to-dot distance.

The shape and/or composition of dots can also vary radially, yielding a graded pattern. For bulk scatter centers, for example, a graded pattern can be provided by forming scatter centers with a lower refractive index mismatch compared to the lens bulk material closer to the edges of the dot pattern compared to scatter centers in the center of the dot pattern.

In some embodiments, information can be encoded into the dot pattern. For example, variations in the spacing, size, and/or shape of the dot pattern can be introduced according to a key such that the information can be subsequently read out by someone who has the key. In some cases, information about the wearer can be encoded into the dot pattern, such as their identity and information about their vision.

Figure 7A:
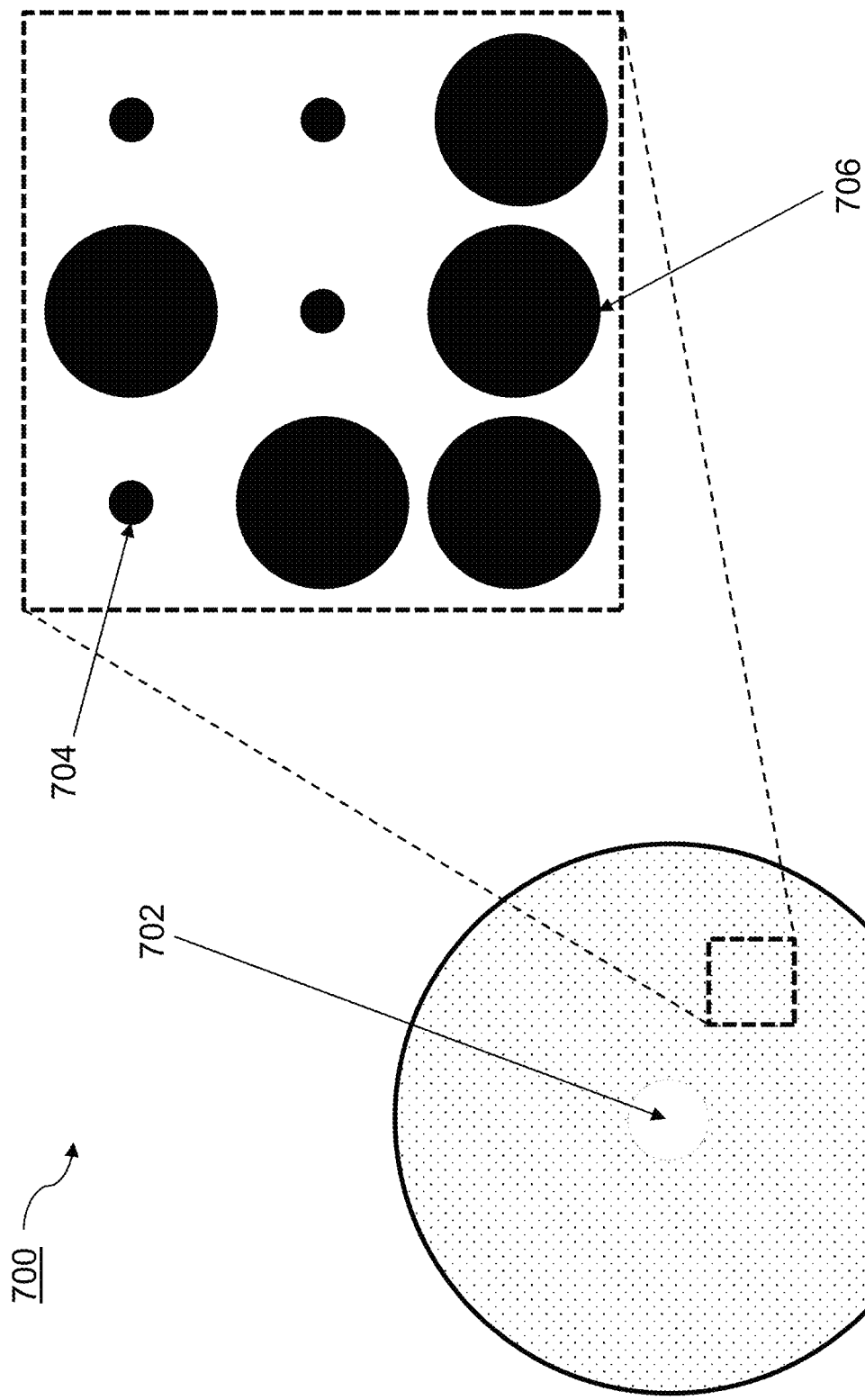
FIG. 7A shows an exemplary lens having a pattern with information encoded by dots of varying size.

In some embodiments, the dots can be dots of varying sizes. Referring to FIG. 7A, a lens 700 includes a clear aperture 702 and a dot pattern that includes dots of different sizes: small dots 704 and large dots 706. In an embodiment, the small dots 704 are small relative to the large dots 706, and accordingly, the large dots 706 are large relative to the small dots 704.

In certain implementations, the small dots 704 and the large dots 706 can correspond to binary components. For example, the small dots 704 correspond to zeros and the large dots 706 correspond to ones, as the intensity of the reflected light off of the small dots 704 and the large dots 706 will be different and can be interpreted as binary code. When read in a string, the small dots 704 and the large dots 706 form a binary code sequence encoded with information including but not limited to the wearer's identity or vision information. For example, the encoded information can include lens prescription information, In certain implementations, there can be additional dot sizes beyond the small dot size 704 and the large dot size 706, e.g., the dot sizes of the dot pattern are not limited to two sizes. For example, a variety of dot sizes can be used that correspond to different outputs when a sensor detects the reflected light from the encoded dot pattern of the lens 700. The sensor can be configured to detect three or more different intensities of the reflected light (e.g., intensities of the reflected light from three or more different dot sizes of the dot pattern on the lens 700).

Figure 7B:
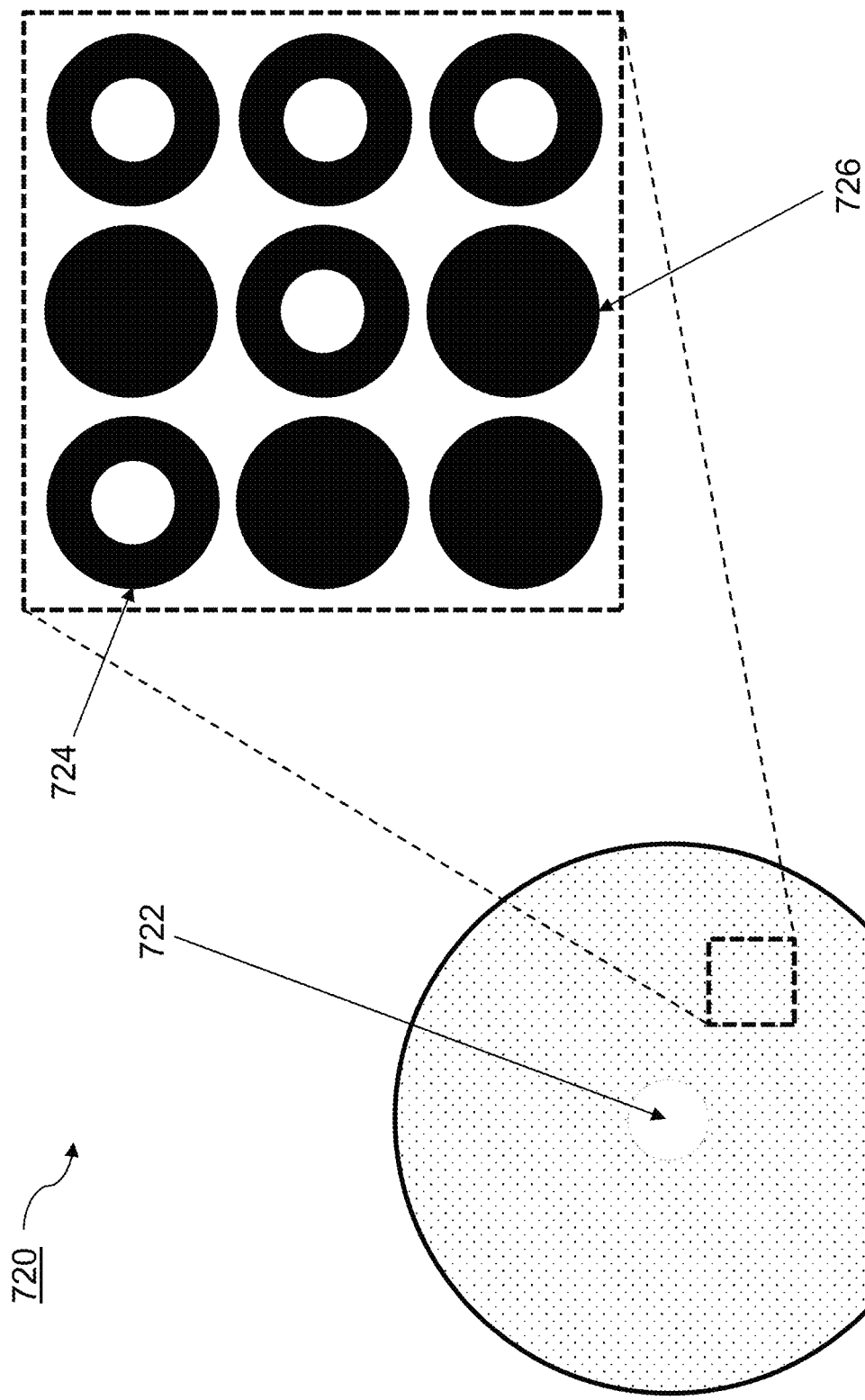
FIG. 7B shows an exemplary lens having a pattern with information encoded by dots having different shapes.

In some embodiments, the dots can be dots of annular rings with varying thickness. Referring to FIG. 7B, a lens 720 includes a clear aperture 722 and a dot pattern that includes "donuts" 724 (e.g., dots with an annular ring and a clear center) and dots 726.

In certain implementations, the donuts 724 and the dots 726 can correspond to binary components. For example, the donuts 724 correspond to zeros and the dots 726 correspond to ones, and when read in a string, the donuts 724 and the dots 726 form a binary code sequence encoded with information including but not limited to the wearer's identity or vision information. For example, the encoded information can include lens prescription information.

In an embodiment, the size, shape, and/or thickness of the annular rings of the donuts 724 varies, and thus, the intensity of the reflected light varies. The sensor can be configured to detect the varying intensities of reflected light to convert into the analog signal that is sent to the decoder. For example, annular rings of certain shapes, sizes, and thicknesses of the donuts 724 can correspond to encoded information that is predefined. For example, an annular ring that has a certain thickness can correspond to a predefined lens prescription strength, and as the thickness of the annular ring increases, the prescription strength of the lens increases.

Figure 7C:
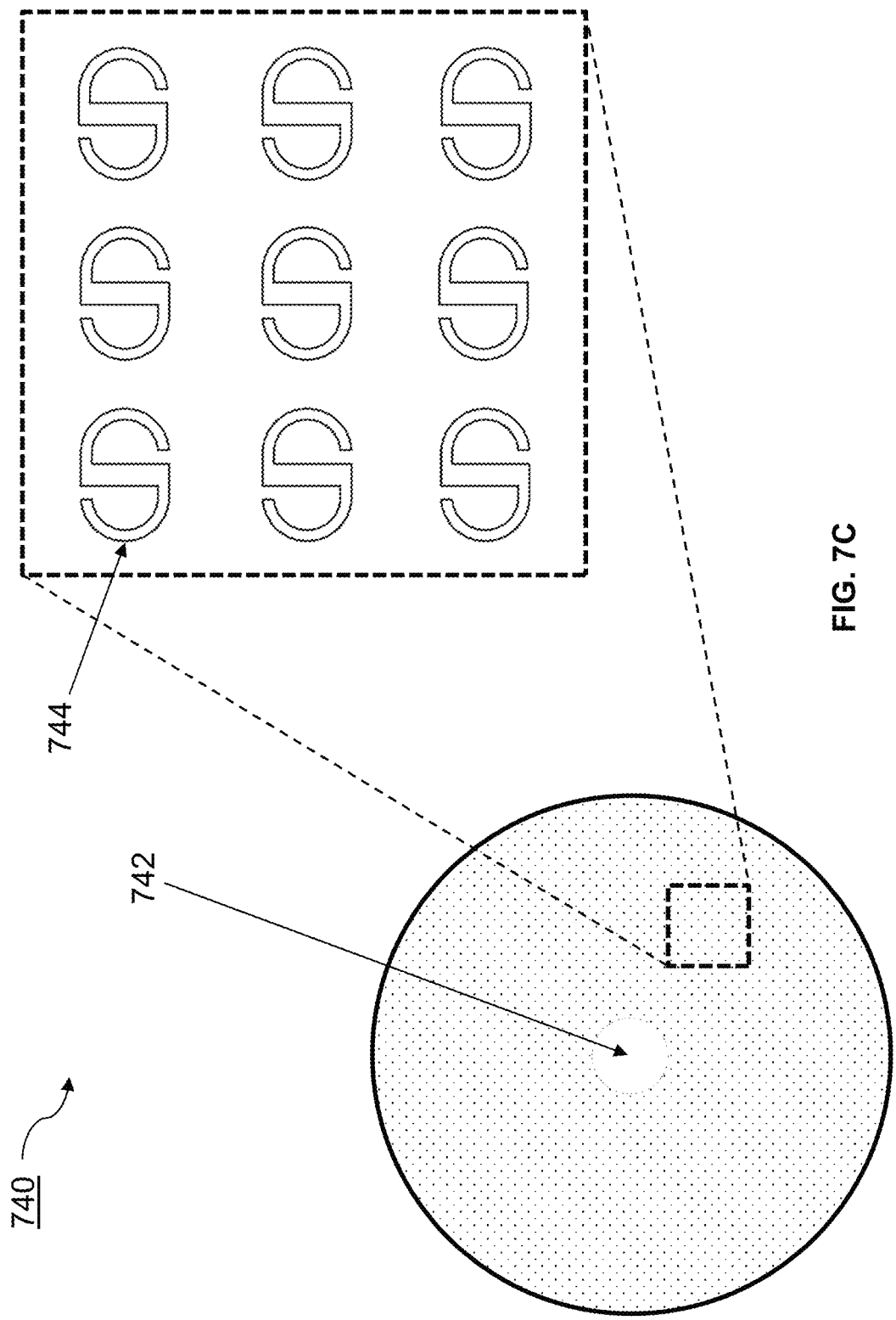
FIG. 7C shows an exemplary lens having a pattern for from dots in the form of a logo.

In some embodiments, the dots can be shaped as symbols, such as alphanumeric symbols or logos. Referring to FIG. 7C, a lens 740 includes a clear aperture 742 and a dot pattern of symbols 744.

In certain implementations, the symbol 744 can be a logo, the same symbol, a variety of symbols, a simple shape, a complex shape, alphanumeric numbers, letters, and/or words. For example, the symbol 744 can be a number indicative of the prescription strength. In another example, the symbol 744 can be a logo of a manufacturer to indicate where replacement lens should be ordered from. In another example, the symbol 744 can be a shape that indicates the diagnosis of the particular wearer (e.g., ovals of varying meridian lengths and heights that correspond to the wearer's levels of myopia and astigmatism).

Generally, variations in the dot spacing, size and/or shape is imperceptible to unaided human vision and magnifying optics and/or a machine reading system is used to read out the encoded information. In certain implementations, a microscopic reader is used to read out the encoded information. For example, a microscope or similar magnifying optic is used to enable an optometrist or a lens technician to read the encoded information from the lens.

Figure 8:
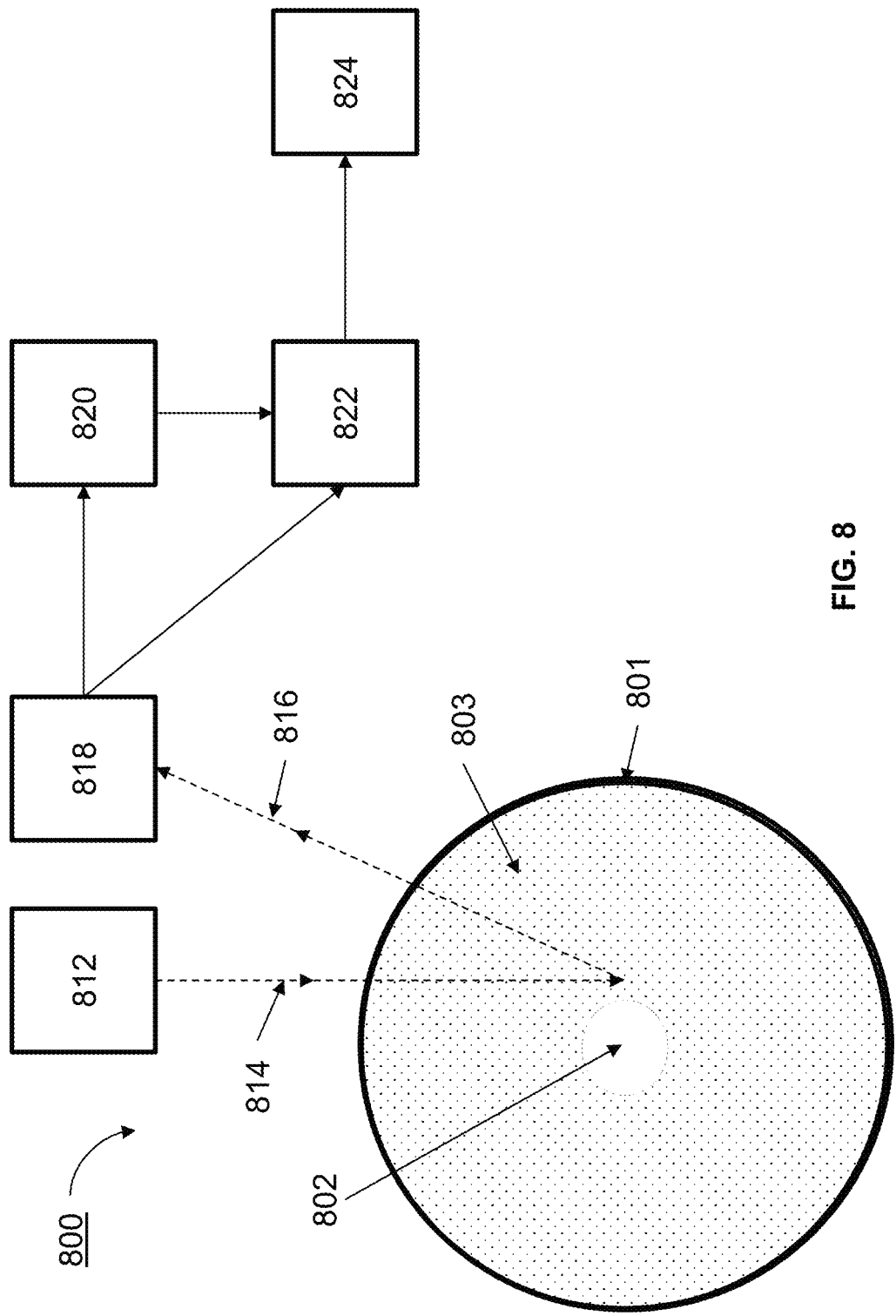
FIG. 8 shows an exemplary machine reading system.

In certain implementations, a machine reading system is used to read out encoded information. Referring to FIG. 8, the machine reading system 800 includes a lens 801 with a clear aperture 802 surrounded by a dot pattern 803, a light emitter 812, light 814, reflected light 816, a sensor 818, a database 820, a decoder circuit 822, and a controller 824.

In some implementations, the system 800 includes a light emitter 812. For example, the light emitter 812 shines a light 814 such as an LED or laser onto the dot pattern 803. The dot pattern 803 is, for example, the encoded patterns illustrated in FIGS. 7A-7C.

The light 814 is (or is not) reflected off of the dot pattern 803 in the form of reflected light 816. The reflected light 816 varies in intensity (e.g., it ranges from no reflection to 100% reflection), as certain dots or the absence of dots can lead to full reflection or no reflection of the light 814. The reflected light 816 can also be a partial reflection of the light 814. Similarly, in some embodiments, transmitted light or a combination of transmitted and reflected light can be used to read out the encoded information In certain embodiments, the system 800 includes a sensor 818. For example, the sensor 818 is a light-detector such as a photoelectric cell. Various implementations of the sensor 818 can include but are not limited to laser scanners and camera-based readers. The sensor 818 detects and measures the intensities of the reflected light 816, and outputs a signal. For example, the signal output by the sensor 818 is an analog signal that represents the intensity of the reflected light 816. The signal generated by sensor 818 corresponding to the intensities of reflected light 816 are output to the decoder circuit 822. For example, the intensities of reflected light 816 can be translated to signals such as on-off pulses.

In some implementations, the signal generated by the sensor 818 is transmitted to the database 820. For example, the database 820 can cross-reference symbols (i.e., perform an image recognition search of symbols, e.g., from FIG. 7C) to decode the signal. The database 820 may contain a bank of symbols, images, alphanumeric code, etc. For example, if the dot pattern 803 comprises a complex shape such as a logo or symbol, the sensor can transmit the signal related to that complex shape to the database 820 for cross-referencing.

In an embodiment, the decoder circuit 822 decodes the signal from the sensor 818 and translates it into a digital signal. The digital signal is the digital representation of the signal from the sensor 818, such as, for example, binary code with zeros representing the off pulses and ones representing the on pulses.

The decoder circuit 822 transmits the digital signal to the controller 824. The digital signal can be read by the controller 824. For example, the decoder circuit 822 can transmit binary code that the controller 824 converts into text, and thus, the encoded information on the dot pattern 803 can be read.

While the above embodiments feature examples in which the reduced contrast areas are annular (e.g., a concentric circular surrounding the clear aperture), more generally, other shapes are possible. For example, elongate (e.g., elliptical) shapes are possible. In general, the reduced contrast area can cover the entire lens outside of the clear aperture, or just a portion leaving a clear lens at the lens' periphery.

In general, dots can be formed from lenses in a variety of ways. For example, dots can be formed using inkjetting techniques, such as those disclosed in PCT/US2017/044635, filed Jul. 31, 2017, entitled "OPHTHALMIC LENSES FOR TREATING MYOPIA," the entire contents of which is incorporated herein by reference.

In some embodiments, dots are formed on a lens by exposing the lens to laser radiation. The laser radiation locally interacts with the lens material, creating a dot. Generally, as discussed in the examples below, lasers can be used to form dots either on a surface of a lens or in the bulk material of the lens. For example, exposure of a lens surface to a laser beam having sufficient energy can create a dot by leaving a small depression and/or roughened patch on the surface. By selectively exposing areas of the lens surface to laser radiation, a dot pattern can be formed on the surface. For example, the laser's beam can be moved relative to the surface while the beam is pulsed. Relative motion between the beam and the lens surface can be caused by moving the beam while leaving the surface fixed, moving the surface while leaving the beam fixed, or moving both the beam and the surface.

Generally, the optical properties of a dot formed using a laser on a lens surface can be influenced in a number of ways. For example, the energy density of a laser beam pulse will generally affect the physical and/or chemical interaction of the laser light with the lens material. For instance, for certain pulse energies, lens material can be melted where it is exposed to form a dot. At some pulse energies, dots can be formed by causing the lens material to foam. This can occur at for higher energies relative to lens melting. For some pulse energies, the interaction between the laser light and the lens material can result in a color change to the lens material (e.g., by charring). In still other instances, lens material can be removed from a lens surface by ablation.

Other laser parameters can also influence the nature of dots formed using the laser. These include the laser wavelength, exposure time (for example, how long each dot location is exposed), and number of passes (e.g., exposing an area multiple times, where other areas are exposed between each), each of which can be selected to achieve a desired surface modification. In addition, the interaction between the laser light and the lens material will depend on the lens material itself. For example, dots in lens materials with lower glass transition temperatures may be formed using lower pulse energies or fewer pulses that comparable dots in a lens material with a relatively higher glass transition temperature.

In some embodiments, the laser and its operating parameters are selected to provide dots that have a particular range of forward scattering angles, for example, between 3 and 30 degrees. In particular, laser parameters can be chosen to achieve surface modifications that lead to a forward scattering angle of 15.5 to 19.5 degrees. In certain cases, laser parameters are chosen to achieve scattering efficiency (e.g., haze) of 10-50%. In particular, laser parameters can be chosen to achieve scattering efficiency of 15% to 19%, and 38% to 42%.

The resolution of the laser beam at the lens surface can be smaller than the desired dot size. For instance, the beam resolution (e.g., as determined from the FWHM of the intensity profile) can be about 50% of the dimension of the dot or less (e.g., about 25% or less, about 10% or less, about 5% or less, about 1% or less). In some embodiments, the beam can be capable of forming features having a dimension of 100 µm or less (e.g., 50 µm or less, 20 µm or less, 10 or less, 5 µm or less).

Figure 9:
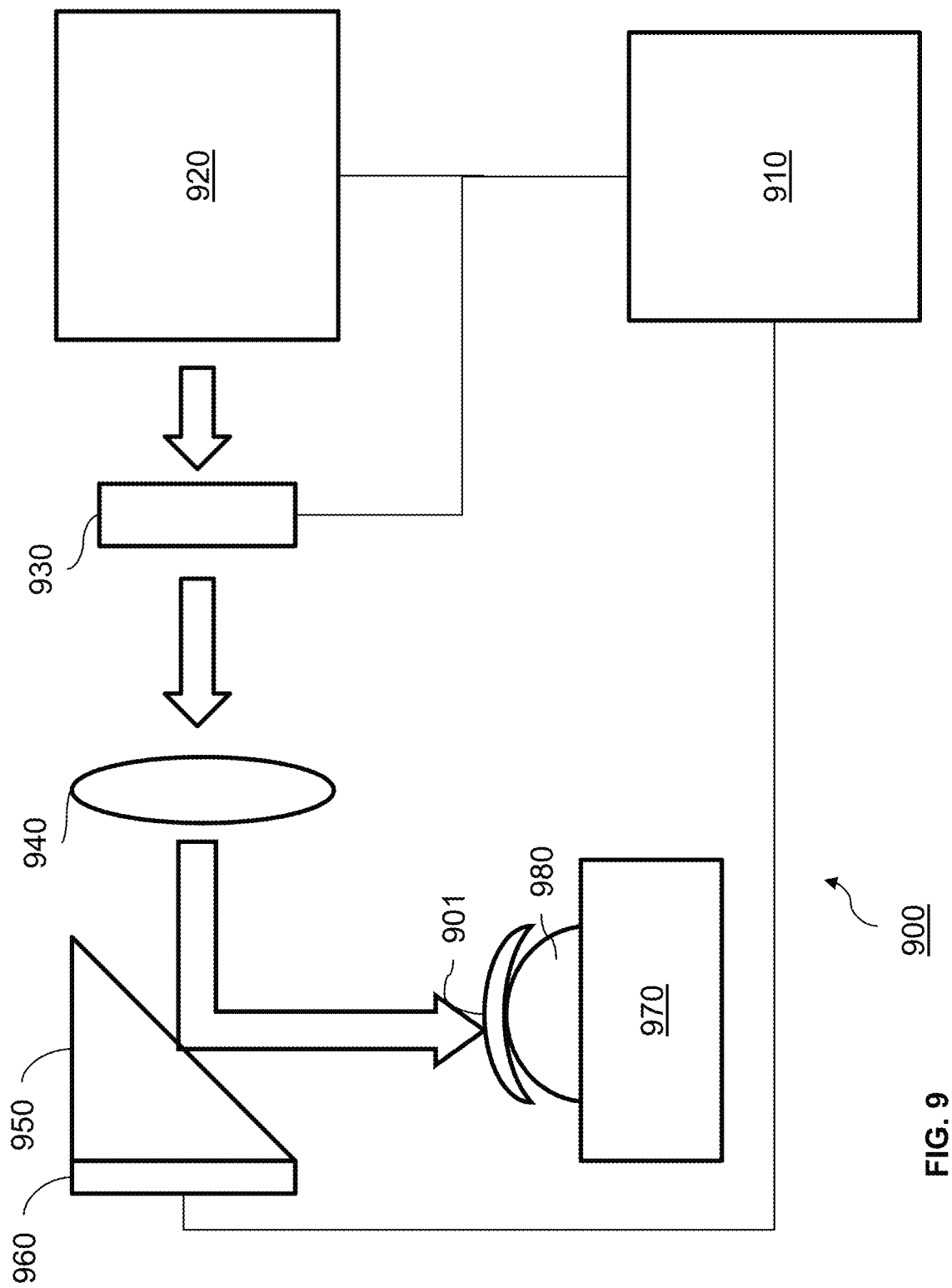
FIG. 9 is a schematic diagram of a laser system for forming recesses on a surface of a lens.

Referring to FIG. 9, a laser system 900 for forming dots on a surface of a lens includes a laser 920, a beam chopper 930, focusing optics 940, a mirror 950, and a stage 970. Laser 920 directs a laser beam towards mirror 950, which deflects the beam towards a lens 901 which is positioned relative to the mirror 950 by stage 970. An actuator 960 (e.g., a piezoelectric actuator) is attached to mirror 950. The stage includes a lens mounting surface 980 which supports lens 901. Laser system 900 also includes a controller (e.g., a computer controller) in communication with laser 920, beam chopper 930, and actuator 960.

Beam chopper 930 and focusing optics 940 are positioned in the beam path. Chopper 930 periodically blocks the beam so that lens 901 is exposed to discrete pulses of laser light. Focusing optics 940, which generally includes one or more optically powered elements (e.g., one or more lenses), focuses the beam to a sufficiently small spot on the surface of lens 901 so that the area ablated by the beam on the lens surface corresponds to the desired dot size. Actuator 960 changes the orientation of mirror 950 with respect to the beam to scan the pulsed beam to different target points on the lens surface. Controller 910 coordinates the operation of laser 920, chopper 930, and actuator 960 so that the laser system form a predetermined dot pattern on the lens.

In some implementations, stage 970 also includes an actuator. The stage actuator can be a multi-axis actuator, e.g., moving the lens in two lateral dimensions orthogonal to the beam propagation direction. Alternatively, or additionally, the actuator can move the stage along the beam direction. Moving the stage along the beam direction can be used to maintain the exposed portion of the lens surface at the focal position of the beam, notwithstanding the curvature of the lens surface, thereby maintaining a substantially constant dot size across the lens surface. The stage actuator can also be controlled by controller 910, which coordinates this stage motion with the other elements of the system. In some embodiments, a stage actuator is used in place of the mirror actuator.

Generally, laser 920 can be any type of laser capable of generating light with sufficient energy to ablate the lens material. Gas lasers, chemical lasers, dye lasers, solid state lasers, and semiconductor lasers can be used. In some embodiments, infrared lasers, such as a $CO_2$ laser (having an emission wavelength at 9.4 µm or 10.6 µm) can be used. Commercially-available laser systems can be used such as, for example, $CO_2$ laser systems made by Universal Laser Systems, Inc. (Scottsdale, AZ), (e.g., the 60 W VLS 4.60 system). In some embodiments, femtosecond lasers can be used. For example, a commercial femtosecond laser system such as those made by Trumpf (Santa Clara, CA) (e.g., as the TruMicro 2030 laser device of the TruLaser Station 5005) can be used to form a dot pattern of a desired shape and size. The burst mode of such a laser device can achieve burst energy that is much higher compared to the maximum energy of a single pulse, leading to higher ablation rates. This exemplary laser system can provide pulse duration of less than 400 femtoseconds with 50 µJ maximum pulse energy.

The pulse duration and pulse energy are typically selected to provide a dot of a desired size. For example, in some embodiments, laser 920 forms the predetermined dot pattern on lens 901 by melting the surface of lens 901 (e.g., laser etching). For example, laser 920 heats up and melts a portion of lens 901 surface to form a dot as the laser etching causes the melted material of lens 901 to expand, causing a recessed dimple and a raised well around it that forms the dot.

In certain implementations, laser 920 forms the predetermined dot pattern on lens 901 using laser foaming. For example, when laser light interacts with the lens material, the material softens or melts and gas bubbles form in the softened/molten material. These bubbles become trapped when the material cools down and returns to its room temperature state. The trapped bubbles can efficiently scatter light, providing the dots.

In embodiments, laser 920 forms the predetermined dot pattern on lens 901 using laser marking. For example, laser marking forms the predetermined dot pattern on lens 901 by inducing color changes on lens 901, e.g., due to chemical or physical alteration of the portion of the lens 901 that forms the predetermined dot pattern. In another embodiment, the laser 920 forms the predetermined dot pattern on lens 901 by using laser marking to char the lens 901 to form the predetermined dot pattern on lens 901.

In some implementations, laser 920 forms the predetermined dot pattern on lens 901 using ablation. For example, laser 920 is used to ablate (e.g., remove material) lens 901 by evaporating or sublimating lens 901 material locally to form the predetermined dot pattern. After ablation, a crater may form on lens 901.

In some embodiments, to reduce conspicuousness of the dot pattern (e.g., to reduce backward scattering and reflection at the scattering center due to the ablation crater), the surface of the ablation crater on lens 901 is modified to reduce surface roughness. Reducing surface roughness can reduce the effects of small angle light scattering (e.g., where scattering angle is less than 3 degrees). For example, the surface of an ablation crater on lens 901 can be modified by second pass to melt the rough surface of the ablation crater (e.g., by using a lower energy beam). The lower energy beam can be achieved, for example, by defocusing laser 920 (e.g., by increasing laser 920 beam width). In some implementations, continuing to reduce conspicuous of the dot pattern involves defocusing laser 920 over multiple iterations. For example, defocusing laser 920 occurs in several passes (e.g., with each second, third, fourth, etc. pass) with increased defocusing (e.g., increasing beam width with each pass) to influence conicity of the crater (e.g., feathering or smoothing the crater edge). In some implementations, reducing conspicuousness of the dot pattern involves multiple overlapping ablations being performed to compose one ablation crater with multiple overlapping ablation craters, e.g., two or more overlapping concentric circles.

In some implementations, reducing conspicuousness of the dot pattern involves coating an anti-reflective layer on the back surface of lens 920. In some implementations, a reflective layer is coated on the lens front surface. This is particularly beneficial if the laser ablation is performed on the back surface of lens 901. Generally, laser 920 has a stronger impact on the coating than the lens 901 material, thus influencing conicity of the crater (e.g., feathering or smoothing of the crater edge).

In some embodiments, focusing optics with a small depth of focus can be used in conjunction with the curvature of the lens surface to provide varying dot size across the lens's surface. For example, referring to FIG. 10 and similar to system 900, a laser system 1000 for forming dots on a surface of a lens 1001 includes a laser 1020, a beam chopper 1030 (or other modulator for generating laser pulses), focusing optics 1040, a mirror 1050, and a stage 1080. Laser 1020 directs a laser beam 1025 towards mirror 1050, which deflects the beam 1025 towards a lens 1001 which is positioned relative to the mirror 1050 by stage 1080. An actuator 1060 is attached to mirror 1050. Laser system 1000 also includes a controller 1010 in communication with laser 1020, beam chopper 1030, actuator 1060.

Beam chopper 1030 and focusing optics 1040 are positioned in the beam path. Chopper 1030 periodically blocks beam 1025 so that lens 1001 is exposed to discrete pulses of laser light. Focusing optics 1040 focuses beam 1025 to a sufficiently small spot 1045 on or near the surface of lens 1001 so that the area ablated by beam 1025 on the lens surface corresponds to the desired dot size. Actuator 1060 changes the orientation of mirror 1050 with respect to beam 1025 to scan the pulsed beam 1025 to different target points on the lens surface. Controller 1010 coordinates the operation of laser 1020, chopper 1030, and actuator 1060 so that the laser system 1000 forms a predetermined dot pattern on lens 1001.

Figure 10:
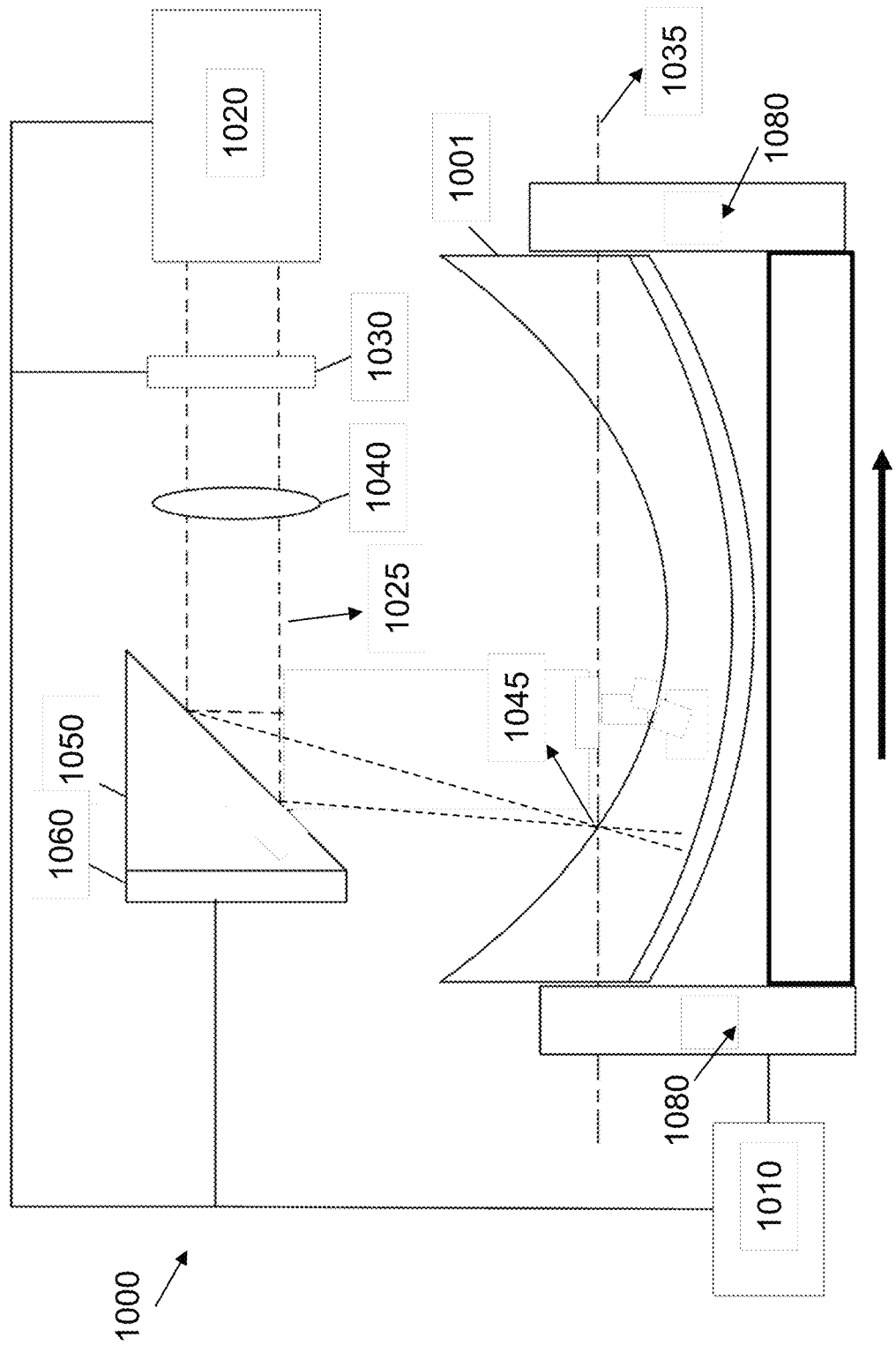
FIG. 10 is a schematic diagram of another laser system for forming recesses on a surface of a lens.

Moving stage 1080 moves lens 1001 laterally parallel to a focal plane 1035 of laser beam 1025 as indicated by the arrow in FIG. 10. Due to the curvature of the lens surface, the lens surface will not always coincide with the focal plane 1035 at the focal spot 1045 of the laser beam, meaning that the intensity of the laser radiation at the lens surface will vary depending on the lateral position of the lens with respect to spot 1045. Generally, the amount the lens surface is etched will depend on the intensity of the laser radiation it receives. Accordingly, positions on the lens surface exposed to an out-of-focus beam receive less intensive etching than those positions where the lens surface coincides with focal plane 1035. The result, assuming the laser pulse time and lateral translation velocity are constant, is that the etch rate will be highest at the position where the lens surface coincides with the focal plane 1035 and will be reduced the further the lens is translated from this location. Accordingly, a graded pattern can be achieved simply based on the curvature of the lens surface.

Of course, other exposure parameters (e.g., pulse time, pulse energy, dot composition such as where a dot is formed by multiple overlapping or nearby ablation centers, foamed or melt zones) can be used along with, or separate from, the lens curvature to achieve a desired graded dot pattern.

Figure 11A:
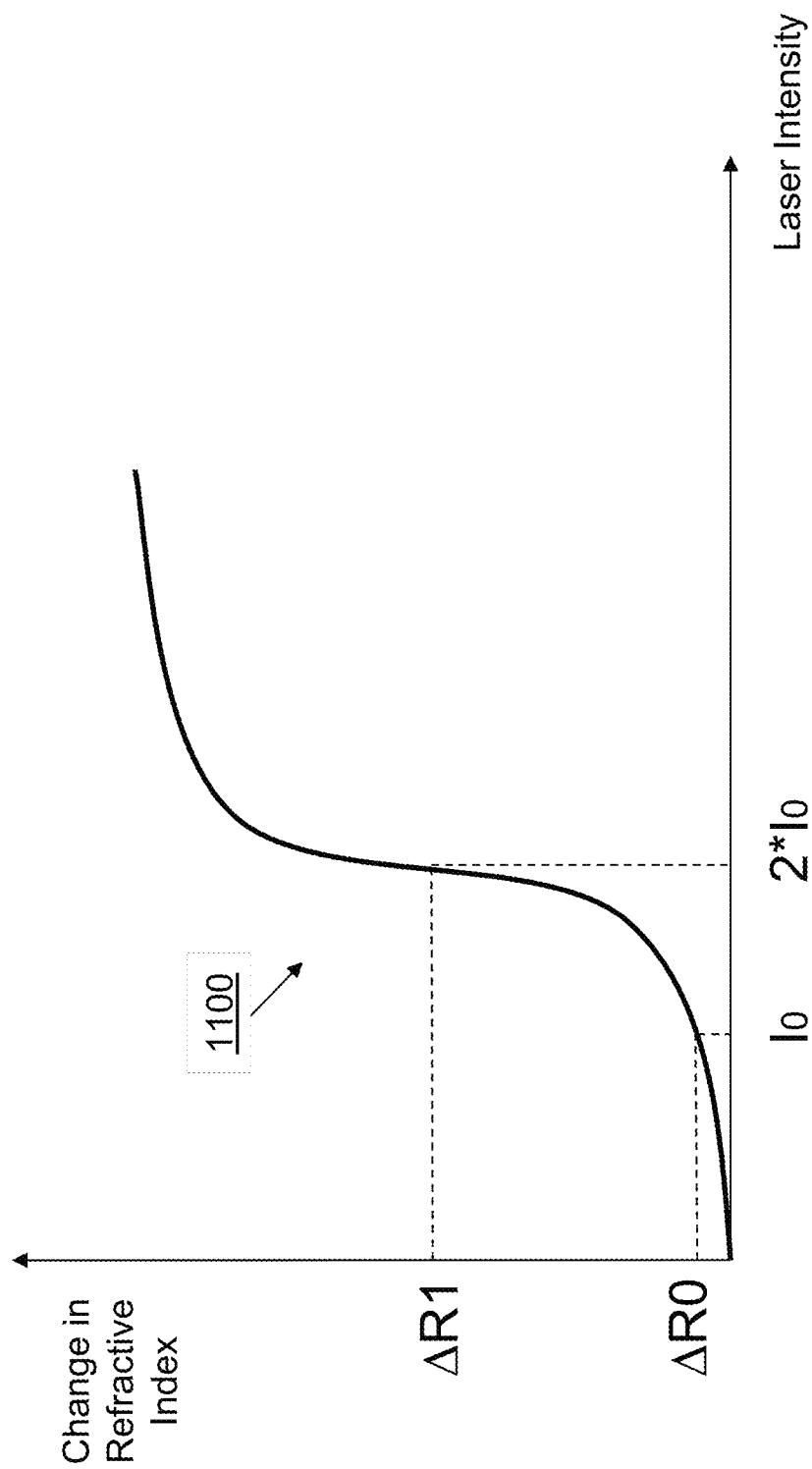
FIG. 11A is a plot of change in refractive index of lens material versus laser intensity.

Laser systems can also be used to form scattering centers in the bulk material of the lens. In many cases, the effect of laser radiation of the bulk properties of an optical material (e.g., a plastic or glass) depends on the intensity of the laser radiation. These changes can occur via one or more different mechanisms, such as a photochemical change, a photothermal change (e.g., the light causes heating, which changes the properties of the material), and/or some other mechanism. Generally, the greater the intensity, the greater the change in the optical material will be. In many cases, this change is not necessarily a linear relationship. For instance, there may exist some threshold intensity, below which, little if any change in the bulk material occurs. At some threshold intensity, changes begin to take place. For example, referring to FIG. 11A, a plot of such a non-linear relationship between refractive index change in a lens material versus laser intensity is shown.

Laser radiation with relatively low intensity $I_0$ produces only a small change in refractive index $\Delta R_0$; however, when laser intensity reaches $2I_0$, a significant change in refractive index $\Delta R_0$ occurs.

This non-linear behavior of refractive index change can be used to localize embedded scattering centers in lens material. For example, a lens can be exposed to two or more laser beams each with beam intensity less than a threshold intensity for causing a significant refractive index change. While each laser beam is too weak to produce a noticeable change in refractive index, regions where the laser beams overlap (e.g. all laser beams can focus on the same point) can experience a sufficient change in refractive index, corresponding to the creation of a scattering center. Alternatively, optics with a narrow focal zone can be used to if the beam focus is placed within the bulk of the material.

Figure 11B:
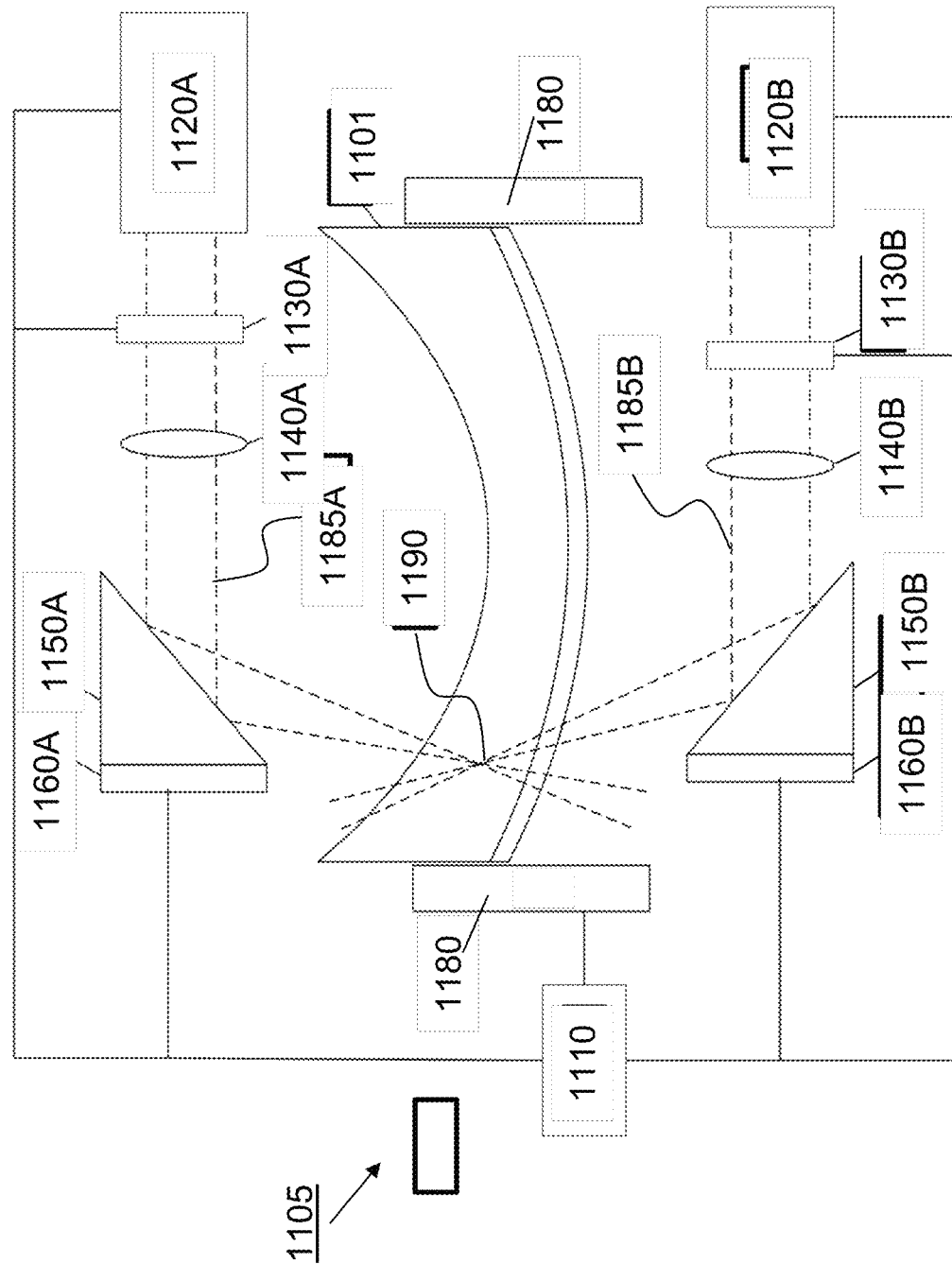
FIG. 11B is a schematic diagram of a laser system for forming inclusions in the bulk materials of an exemplary lens.

For example, referring to FIG. 11B, a laser system 1105 producing embedded scattering centers in a lens 1101 using two overlapping beams is shown. Laser system 1105 includes two lasers 1120A and 1120B, beam choppers 1130A and 1130B, focusing optics 1140A and 1140B, mirrors 1150A and 1150B, actuator 1160A and 1160B, and stage 1180. A controller 1110 is connected to each of the actuators, focusing optics, and lasers. Each laser is operated in a manner similar to that described in FIG. 10. The focusing optics and mirrors are configured to focus beams 1185A and 1185B to a common region 1190 inside lens 1101, where the intensity of the overlapping beams is sufficient to effect a change in the lens material sufficient to form a scattering center. Outside the region of overlap, the intensity rapidly falls off to a value below any threshold for significant refractive index change.

More than two lasers can be used. Alternatively, or additionally, a beam from a single laser can be split and separately directed to the lens so that they overlap at a target region, producing a scattering center.

Other arrangements are also possible. For example, multiple laser beams can enter the lens from the same surface, rather than from opposite surfaces as depicted in FIG. 11B.

While the foregoing description pertains to ophthalmic lenses for eyeglasses, the principles disclosed may be applied to other forms of ophthalmic lenses, such as contact lenses. In some embodiments, dot patterns may be provided on contact lenses to provide similar therapeutic effects. The size and spacing of dots in a contact lens dot pattern may be sized so that they subtend comparable solid angles in a user's visual field to the dot patterns described for eyeglass lenses above.

EXAMPLES

Dots were formed on Trivex lenses using a Trumpf Trumark 5000 marking laser station, equipped with a nanosecond UV laser at a pulse repetition rate of 20 kHZ. The laser station was operated at a scan speed of 1,000 mm/s and 100% output power. The dots were approximately 170 microns in diameter and yielded a haze of 15% to 42% depending on dot spacing. In some instances, the dots were formed by marking two concentric overlapping circles with radii of about 0.06 mm and 0.03 mm, composed of individual laser marks of about 0.04 mm in diameter, yielding a dot with an overall diameter of 0.17 mm. Adjacent dots were spaced either 0.24 mm or 0.365 mm apart.

Other Embodiments

A number of embodiments are described. Other embodiments are in the following claims.

What is claimed is:

1. A method, comprising:
forming, on an ophthalmic lens, a plurality of spaced apart scattering centers sized and shaped to scatter light incident on the ophthalmic lens,
wherein the scattering centers are formed in a pattern such that each scattering center is the located at or near a corresponding array site of a two-dimensional array in which the spacing between array sites is a first distance, $D_x$, in one direction in a plane of the array and a second distance, $D_y$, in a second direction in the plane of the array, the second direction being orthogonal to the first direction,
wherein a center of each scattering center is displaced from a corresponding array site by an amount $\delta x$ in the first direction and by an amount $\delta y$ in the second direction, where $\delta x = A_x \cdot D_x \cdot RN[0,1]$, and $\delta y = A_y \cdot D_y \cdot RN[0,1]$, wherein $A_x$ and $A_y$ are amplitudes that are between 0 and 1 and RN is a random number between 0 and 1.

2. The method of claim 1, wherein the scattering centers are formed on a surface of the ophthalmic lens.

3. The method of claim 1, wherein the scattering centers are formed in a bulk of the ophthalmic lens.

4. The method of claim 1, wherein forming the scattering centers comprises exposing the ophthalmic lens to laser radiation.

5. The method of claim 1, wherein forming the scattering centers comprises inkjetting a material on a surface of the ophthalmic lens.

6. The method of claim 1, wherein scattering centers are formed in a scattering region surrounding a clear aperture in the ophthalmic lens.

7. The method of claim 6, wherein the ophthalmic lens comprises a lens axis and the clear aperture and scattering region are substantially centered on the lens axis.

8. The method of claim 6, wherein the scattering region comprises a first scattering area and a second scattering area arranged between the clear aperture and the first scattering area, the second scattering area comprising scattering centers sized and arranged to scatter incident light more weakly than the scattering centers of the first scattering area.

9. The method of claim 6, wherein the scattering region is an annular region.

10. The method of claim 6, wherein the clear aperture is a circular aperture.

11. The method of claim 1, wherein spacing between array sites is in a range from 0.2 mm to 1 mm.

12. The method of claim 1, wherein the scattering centers have a maximum dimension in a plane of the array in a range from 0.08 mm to 0.5 mm.

13. The method of claim 1, wherein at least some of the scattering centers have a dimension in the plane of the array that varies from the dimension of other of the scattering centers.

14. The method of claim 13, wherein a variation of the dimension of the at least some scattering centers in the plane of the array is 0.5 times or less than a nominal value.

15. The method of claim 1, wherein at least some of the scattering centers have a volume that varies from a volume of other of the scattering centers.

16. The method of claim 15, wherein a variation of the volume of the at least some scattering centers is 0.5 times a nominal value or less.

17. The method of claim 15, wherein the pattern comprises irregular variations in scattering center size.

18. The method of claim 1, wherein the scattering centers are substantially circular in shape in the plane of the array.

19. The method of claim 1, wherein the ophthalmic lens is one of a plano lens, a single vision lens, and a multivision lens.

20. The method of claim 1, wherein the ophthalmic lens is one of an eyeglass lens and a contact lens.

* * * * *